US008113199B2

(12) United States Patent
Augustyn et al.

(10) Patent No.: US 8,113,199 B2
(45) Date of Patent: Feb. 14, 2012

(54) COUNTER FOR USE WITH A MEDICAMENT DISPENSER

(75) Inventors: Stephen Edward Augustyn, Milton Keynes (GB); Stephen James Harvey, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 980 days.

(21) Appl. No.: 10/597,551

(22) PCT Filed: Feb. 15, 2005

(86) PCT No.: PCT/GB2005/000531
§ 371 (c)(1),
(2), (4) Date: Jul. 28, 2006

(87) PCT Pub. No.: WO2005/079727
PCT Pub. Date: Sep. 1, 2005

(65) Prior Publication Data
US 2009/0139516 A1 Jun. 4, 2009

(30) Foreign Application Priority Data

Feb. 16, 2004 (GB) .................................. 0403394.0
Aug. 16, 2004 (GB) .................................. 0418264.8

(51) Int. Cl.
*A62B 9/00* (2006.01)
*B67D 7/22* (2010.01)
*G07F 11/00* (2006.01)
(52) U.S. Cl. ........................ 128/205.23; 222/24; 221/7
(58) Field of Classification Search .......... 128/200.14–200.24, 203.12, 203.15, 128/203.19, 203.21, 205.23; 222/36, 38, 222/24; 116/307, 311, 312, 317, 318; 235/1 A, 235/24; 221/2, 6–8, 17
See application file for complete search history.

(56) References Cited

U.S. PATENT DOCUMENTS

| 2,550,103 | A | * | 4/1951 | White ........................... 235/1 A |
| 3,818,689 | A | | 6/1974 | Muller |
| 4,668,218 | A | | 5/1987 | Virtanen |
| 4,940,966 | A | | 7/1990 | Pettigrew et al. |
| 5,482,030 | A | | 1/1996 | Klein |

(Continued)

FOREIGN PATENT DOCUMENTS

BE 500836 A 4/1952

(Continued)

*Primary Examiner* — Justine Yu
*Assistant Examiner* — Valerie L Skorupa
(74) *Attorney, Agent, or Firm* — James P. Riek

(57) ABSTRACT

There is provided a dose counter for use with a medicament dispenser. The dose counter comprises a first count wheel arranged to rotate about a first axis of rotation, the first count wheel including a set of primary drive teeth arranged annularly thereon for drivable rotation of the first count wheel about the first axis of rotation; a second count wheel arranged to rotate about the first axis of rotation, the second count wheel including a set of secondary drive teeth arranged annularly thereon; and a kick wheel arranged to rotate about a second axis of rotation offset from the first axis of rotation, the kick wheel including a set of kick teeth arranged annularly thereon and in meshed relationship with the set of secondary drive teeth of the second count wheel such that rotary motion of the kick wheel results in rotary motion of the second count wheel. The first count wheel further includes a fixed index tooth arranged for intermittent meshing with the kick teeth of the kick wheel such that rotary motion of the kick wheel results from rotary motion of the first count wheel only when the intermittent meshing occurs.

27 Claims, 25 Drawing Sheets

U.S. PATENT DOCUMENTS

| | | | |
|---|---|---|---|
| 5,590,645 A | 1/1997 | Davies et al. | |
| 5,657,748 A | 8/1997 | Braithwaite | |
| 5,687,710 A | 11/1997 | Ambrosio et al. | |
| 5,740,792 A | 4/1998 | Ashley et al. | |
| 5,860,419 A | 1/1999 | Davies et al. | |
| 5,873,360 A | 2/1999 | Davies et al. | |
| 5,988,496 A | 11/1999 | Bruna | |
| 6,041,779 A | 3/2000 | Juusela | |
| 6,076,521 A * | 6/2000 | Lindahl et al. | 128/203.15 |
| 6,082,358 A | 7/2000 | Scarrott et al. | |
| 6,142,339 A | 11/2000 | Blacker et al. | |
| 6,161,724 A | 12/2000 | Blacker et al. | |
| 6,164,494 A | 12/2000 | Marelli | |
| 6,182,655 B1 | 2/2001 | Keller et al. | |
| 6,234,168 B1 | 5/2001 | Bruna | |
| 6,240,918 B1 | 6/2001 | Ambrosio et al. | |
| 6,283,365 B1 | 9/2001 | Bason | |
| 6,328,037 B1 | 12/2001 | Scarrott et al. | |
| 6,336,453 B1 | 1/2002 | Scarrott et al. | |
| 6,360,739 B1 * | 3/2002 | Rand et al. | 128/200.23 |
| 6,431,168 B1 | 8/2002 | Rand et al. | |
| 6,435,372 B1 | 8/2002 | Blacker et al. | |
| 6,446,627 B1 | 9/2002 | Bowman et al. | |
| 6,484,717 B1 | 11/2002 | Dagsland et al. | |
| 6,561,384 B2 | 5/2003 | Blacker et al. | |
| 6,583,040 B1 | 6/2003 | Lin | |
| 6,659,307 B1 | 12/2003 | Stradella | |
| 6,752,153 B1 | 6/2004 | Eckert | |
| 6,769,601 B2 | 8/2004 | Haikarainen et al. | |
| 7,004,164 B2 | 2/2006 | Scarrott | |
| 7,093,594 B2 * | 8/2006 | Harrison et al. | 128/203.15 |
| 2002/0047021 A1 * | 4/2002 | Blacker et al. | 222/23 |
| 2003/0172924 A1 * | 9/2003 | Staniforth et al. | 128/200.14 |
| 2004/0255935 A1 | 12/2004 | Bruna | |
| 2005/0087191 A1 | 4/2005 | Morton et al. | |
| 2007/0029341 A1 | 2/2007 | Stradella et al. | |
| 2008/0041877 A1 | 2/2008 | Stradella et al. | |

FOREIGN PATENT DOCUMENTS

| | | |
|---|---|---|
| EP | 1104318 B | 6/2001 |
| EP | 1449557 | 8/2004 |
| FR | 2022212 | 7/1970 |
| GB | 1290484 | 9/1972 |
| GB | 1317315 A | 5/1973 |
| GB | 2364649 A | 2/2002 |
| GB | 2365778 | 2/2002 |
| GB | 2366208 | 3/2002 |
| GB | 2372541 | 8/2002 |
| GB | 2372542 | 8/2002 |
| GB | 2372543 | 8/2002 |
| GB | 2385640 | 8/2003 |
| JP | 4525373 | 10/1970 |
| WO | WO-9212402 | 7/1992 |
| WO | WO-9534874 A | 12/1995 |
| WO | WO-9631790 | 10/1996 |
| WO | WO-9841258 | 9/1998 |
| WO | 9936115 A2 | 7/1999 |
| WO | WO-0131578 | 5/2001 |
| WO | WO-0137909 | 5/2001 |
| WO | 02053295 A1 | 5/2002 |
| WO | WO-02089882 | 11/2002 |
| WO | WO-02091293 | 11/2002 |
| WO | WO-03028792 | 4/2003 |
| WO | 03080162 A1 | 10/2003 |
| WO | 2004001664 A1 | 12/2003 |
| WO | WO-03101514 | 12/2003 |
| WO | WO-04001664 | 12/2003 |
| WO | 2004002559 A1 | 1/2004 |
| WO | WO-2004012801 | 2/2004 |
| WO | WO-2004026380 | 4/2004 |
| WO | WO-2004089451 | 10/2004 |
| WO | WO-2005/002654 A2 | 1/2005 |
| WO | WO-2005/007226 A1 | 1/2005 |
| WO | WO-2005017463 | 2/2005 |
| WO | WO-2005017824 | 2/2005 |
| WO | WO-2005/041850 A | 5/2005 |
| WO | 2005060917 A1 | 7/2005 |
| WO | WO-2005/113044 A1 | 12/2005 |
| WO | WO-2006/032971 A2 | 3/2006 |

* cited by examiner

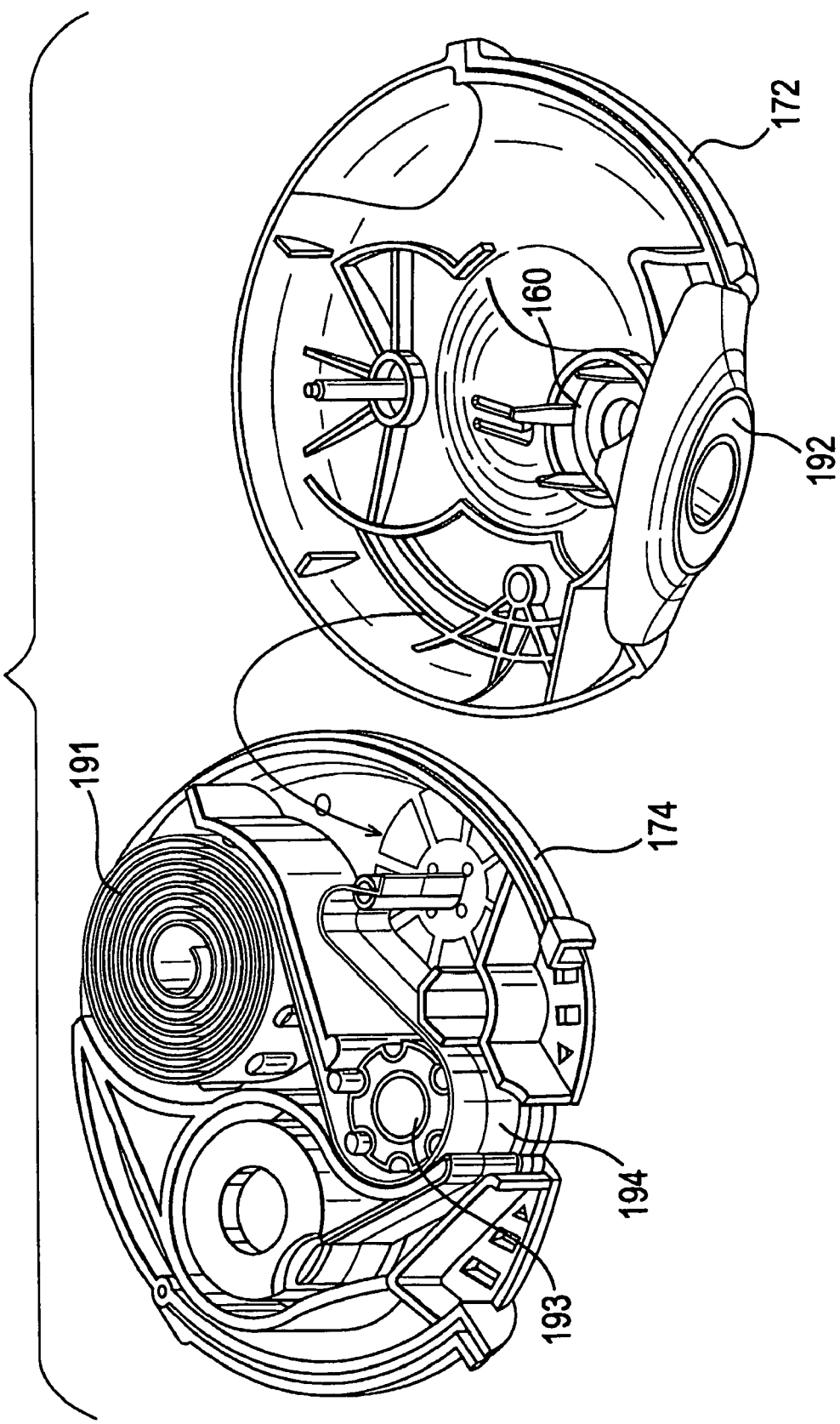

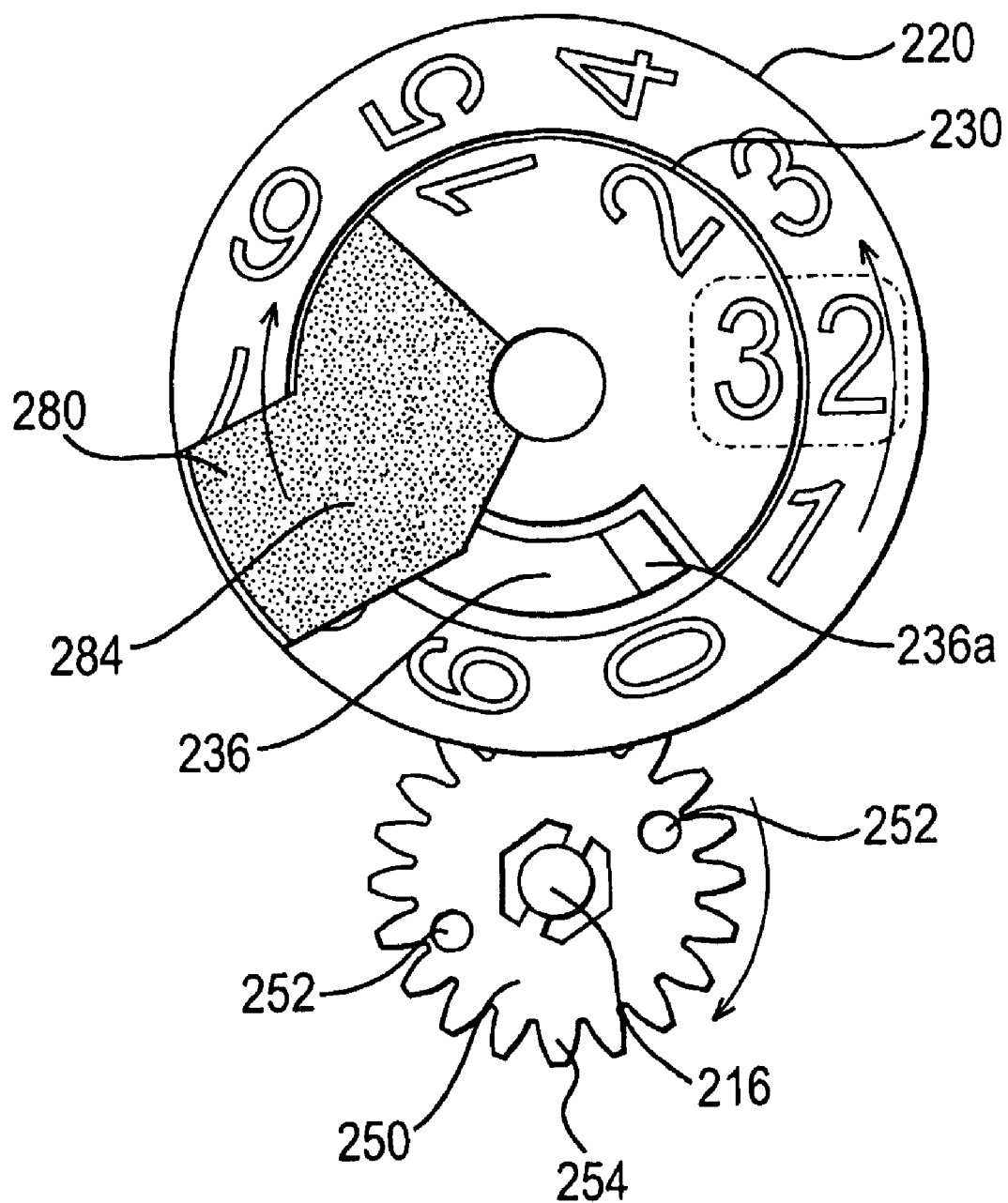

COUNTER FOR USE WITH A MEDICAMENT DISPENSER

CROSS-REFERENCE TO RELATED APPLICATION

This application is filed pursuant to 35 U.S.C. §371 as a U.S. National Phase Application of International Applicaton No. PCT/GB2005/000531 filed Feb. 15, 2005, which claims priority from GB0403394.0 filed Feb. 16, 2004 and GB0418264.8 filed Aug. 16, 2004.

TECHNICAL FIELD

The present invention relates to a counter for use in a medicament dispenser for dispensing individual doses of medicament.

BACKGROUND TO THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister strip containing a number of discrete doses of powdered medicament. Such devices usually contain a mechanism of accessing these doses, usually comprising either piercing means or means to peel a lid sheet away from a base sheet. The powdered medicament can then be accessed and inhaled. Other known devices include those in which the medicament is delivered in aerosol form, including the well known metered dose inhaler (MDI) delivery devices. Liquid-based inhaler devices are also known.

It is advantageous to provide the patient with a dose counter for counting the number of doses of medicament dispensed or still remaining. For flexibility, the dose counter should also be suitable for use with various types of medicament dispenser including those suitable for dispensing medicament in powder or aerosol form. It is also desirable that any counter be configured to register a count only when medicament is provided to the patient for inhalation, and in particular that opportunities for false counts and/or tampering are minimised. It is further desirable that the count be clearly visible by the patient.

The Applicants have now devised a dose counter that meets some or all of the above criteria. In embodiments, the dose counter may be provided to the medicament dispenser as a separable unit, which enables ready re-use and recycling thereof. The latter benefit is particularly important where the counter comprises components, which are readily re-usable and potentially expensive to re-manufacture.

U.S. Pat. No. 5,988,496 describes a dose counter comprising a first count wheel and second count wheel arranged to rotate about a common axis of rotation. The first count wheel includes a drive tongue that is movable between a rest position, in which it does not co-operate with the second count wheel and a drive position, in which it co-operates with the second count wheel to cause it to rotate about the common axis of rotation. The drive tongue is forced into position by action of a cam.

SUMMARY OF THE INVENTION

According to one aspect of the invention there is provided a dose counter for use with a medicament dispenser, said dose counter comprising a first count wheel arranged to rotate about a first axis of rotation, said first count wheel including a set of primary drive teeth arranged annularly thereon for drivable rotation of the first count wheel about said first axis of rotation;

a second count wheel arranged to rotate about the first axis of rotation, said second count wheel including a set of secondary drive teeth arranged annularly thereon; and a kick wheel arranged to rotate about a second axis of rotation offset from the first axis of rotation, said kick wheel including a set of kick teeth arranged annularly thereon and in meshed relationship with the set of secondary drive teeth of the second count wheel such that rotary motion of the kick wheel results in rotary motion of the second count wheel, wherein said first count wheel further includes a fixed index tooth arranged for intermittent meshing with the kick teeth of the kick wheel such that rotary motion of the kick wheel results from rotary motion of the first count wheel only when said intermittent meshing occurs.

By 'arranged annularly' herein it means arranged about a common radius (i.e. to defining an annular arrangement).

Suitably, the dose counter includes a housing, which in aspects includes a bezel/lens cover for the count wheels and through which indicia are generally visible.

The dose counter herein comprises a first count wheel arranged to rotate about a first axis of rotation. The first count wheel may for example, take the form of a disc or a ring.

The first count wheel includes a set of primary drive teeth arranged annularly, preferably circumferentially thereon. The primary drive teeth are therefore arranged in annular fashion at or about the circumference of the first count wheel.

The primary drive teeth are arranged for drivable rotation of the first count wheel about the first axis of rotation. Typically, the drive teeth are in meshed relationship with a drive wheel provided to the medicament dispenser in which the counter is located, wherein the drive wheel is drivable in response to user action (e.g. manual).

The dose counter also includes a second count wheel arranged to rotate about the first axis of rotation. That is to say, both the first and second count wheels rotate about the same (i.e. common) first axis of rotation.

In aspects, the first and second wheels may be arranged to rotate in the same direction or in opposing directions (i.e. one clockwise and one anti-clockwise).

The second count wheel includes a set of secondary drive teeth arranged annularly (e.g. circumferentially) thereon. The secondary drive teeth are therefore arranged in annular fashion at or about the circumference of the second count wheel.

In aspects, the second count wheel is arranged concentric to the first count wheel. In one aspect, the first count wheel takes the form of a ring and the second count wheel (e.g. disc or ring shape) is sized and shaped for receipt within the ring. The diameter of the second count wheel is therefore typically slightly less than that of the inner diameter (i.e. the ring hole diameter) defined by the ring-shaped first count wheel.

In one aspect, the first and second count wheels are arranged concentrically and at the same level (i.e. they share the same plane of rotation).

In another aspect, the first and second count wheels are arranged concentrically and at different levels (i.e. with different planes of rotation).

Suitably, the plane of rotation of the second counter wheel is slightly raised relative to that of the first counter wheel. In one aspect, the second count wheel is provided with a protrusion that in use, extends over and above part of the first count wheel and that may therefore function to shutter off part of the first count wheel.

The dose counter further includes a kick wheel arranged to rotate about a second axis of rotation offset from the first axis of rotation. Preferably, the second axis of rotation is spaced from the first axis of rotation at spacing equivalent to less than the radius of the first count wheel such that the path of rotation defined by the kick teeth of the kick wheel is enclosed by (i.e. within) the path of rotation defined by the primary drive teeth of the first counter wheel.

The kick wheel includes a set of kick teeth arranged annularly, preferably circumferentially thereon. The kick teeth are therefore arranged in annular fashion at or about the circumference of the kick wheel.

The kick teeth are in meshed relationship with the set of secondary drive teeth of the second count wheel such that rotary motion of the kick wheel results in rotary motion of the second count wheel. That is to say, as the kick wheel is rotated the meshing of the kick teeth thereof with the secondary drive teeth of the second count wheel results in rotation of the second count wheel.

The first count wheel further includes a fixed index tooth arranged for intermittent meshing with the kick teeth of the kick wheel. That is to say, the index tooth is fixed to the first count wheel and may be brought into meshed relationship with the kick teeth of the kick wheel on an intermittent basis.

Rotary motion of the kick wheel results from rotary motion of the first count wheel only when said intermittent meshing of the index tooth with the kick teeth occurs. When meshing occurs, a contact ratio of 1 between the index tooth and the kick teeth is preferred, although other whole integer (2, 3, . . . ) contact ratios may be used.

Typically, the index tooth is fixed at a point at or about the circumference of the first count wheel. Rotation of the first count wheel is then arranged to bring the index tooth into meshed relationship with the kick teeth of the kick wheel at a particular point of the rotary cycle of the first count wheel. It may be therefore be appreciated that in this case, meshing occurs once during each complete rotation of the first count wheel.

In aspects, either one or both counter wheels interact with a ratchet mechanism to prevent reverse movement of the counter wheels. This is particularly advantageous when the wheels are contra-rotating in close proximity to one another. The ratchet mechanism may be located on the body of a medicament dispenser within which the counter locates.

In one aspect, the ratchet comprises a cam surface arranged to interact with a cam follower provided to one or both of the count wheels. The cam surface may also be shaped to assist correct alignment of the indicia on the count wheels to provide a clear count reading.

In aspects, a ratchet element is provided on either the first or second count wheels and interacts with a ratchet (e.g. cam) surface locating on the housing. Suitably, the ratchet surface is provided on a lens/bezel provided to the housing and suitably locating above the first and second count wheels.

Suitably, some or all gear teeth of some or all of the toothed parts herein have flanged form to enable effective meshing together thereof.

The dose counter herein is in one aspect, suitable for use with a medicament dispenser of any suitable type and may be provided as an insert thereto.

Suitably, the medicament dispenser has a body, which acts as a housing for the dose counter thereby preventing ingress of dirt or fluid to the mechanism thereof.

The housing suitably includes a viewing window through which the count may be viewed. In one aspect, a shutter is provided to close off the viewing window at a predetermined point, particularly at the 'end of life' of the medicament product, which typically corresponds to the point at which all doses in the normal delivery cycle have been provided. In aspects, the shutter may be provided as a separate element of the dose counter or medicament dispenser or be formed as an integral part of the second counter wheel, as described hereinbefore.

The counter herein is in one aspect, suitable for use with a medicament dispenser for use with a medicament carrier (e.g. having multiple distinct medicament doses carried thereby), said dispenser having an internal mechanism for dispensing the distinct medicament doses carried by said medicament carrier, said mechanism comprising, a) a receiver for receiving the medicament carrier;
b) a releaser for releasing a distinct medicament dose from the medicament carrier on receipt thereof by said receiver;
c) an outlet, positioned to be in communication with the medicament dose releasable by said releaser;
d) an indexer for individually indexing the distinct medicament doses of the medicament carrier; and
e) a dose counter as described hereinbefore for counting each time a distinct medicament dose of the medicament carrier is indexed by said indexer.

Thus, the registration of a count by the dose counter is responsive to indexation by the indexer of a distinct medicament dose from the medicament carrier.

In one aspect, the medicament dispenser is shaped to receive an elongate form medicament carrier. Suitably, the elongate form medicament carrier is in the form of a strip or tape. The term medicament carrier is used to define any suitable carrier. In a preferred aspect, the carrier has a blister pack form, but it could also, for example, comprise a carrier onto which medicament has been applied by any suitable process including printing, painting and vacuum occlusion. The medicament carrier has multiple distinct (i.e. separate) medicament doses carried thereby.

The dispenser has an internal mechanism for dispensing the distinct medicament doses carried by the medicament carrier for administration for inhalation by the patient.

The mechanism comprises a receiver (e.g. a receiving station) for receiving the medicament carrier.

The mechanism further comprises a releaser for releasing a distinct medicament dose from the medicament carrier on its receipt by the receiving station. The releaser can have any suitable form. Where the elongate carrier is in the form of a blister strip, the releaser may for example, be a mechanism to rupture or otherwise access the blister. In a particular preferred aspect, where the blister strip is peelably accessible, the releaser comprises a mechanism for peeling apart the blister strip.

An outlet is positioned to be in communication with the distinct medicament doses releasable by said releaser. The outlet may have any suitable form. In one aspect, it has the form of a mouthpiece and in another, it has the form of a nozzle for insertion into the nasal cavity of a patient.

The outlet is preferably a single outlet, which communicates with the distinct medicament dose releasable by said releaser via a common air channelling means (e.g. formed as an air-pipe or common manifold). The patient may therefore breathe in through a single outlet, and that breath be transferred through the common channelling means to the released medicament dose, thereby enabling its inhalation. Baffles or other mechanical aids to break up released medicament powder may be incorporated. Venturi channelling of the air flow is also envisaged in embodiments. Helical form channels are envisaged.

The mechanism also comprises an indexer for individually indexing the distinct medicament doses carried by the medicament carrier. Said indexing typically happens in sequential fashion, for example accessing dose portions sequentially arranged along the length of the elongate carrier.

The medicament dispenser comprises a counter for counting each time a distinct medicament dose of the medicament carrier is indexed by said indexer. Suitably, indexing by means of the indexer results either directly or indirectly in drivable rotation of the first count wheel of the dose counter herein.

The medicament dispenser may further by provided with means to manipulate, and in particular magnify, an analogue count indicium. The means may in one embodiment, comprise a magnifying window. In another embodiment, the means comprises a prismatic viewer capable of acting on an indicium and causing it to be displayed in manipulated form at a desired viewing position.

In a preferred aspect, the medicament dispenser is suitable for use with a medicament carrier comprising a peelable blister strip having a plurality of pockets for containing medicament wherein said pockets are spaced along the length of and defined between two peelable sheets secured to each other. The respective peelable sheets are generally in the form of a base sheet and a lid sheet of a pocket. In this aspect, the releaser comprises a peeler for peeling apart a base sheet and lid sheet to open a pocket. Suitably, the peeler includes a lid driver for pulling apart a lid sheet and a base sheet of a pocket that has been received at the opening station.

In one aspect, there is provided a medicament dispenser for use with a medicament carrier having multiple distinct pockets for containing medicament doses, wherein said pockets are spaced along the length of and defined between two peelable sheets secured to each other, said dispenser having an internal mechanism for dispensing the medicament doses contained within said medicament carrier, said mechanism comprising,
a) an opening station for receiving a pocket of the medicament carrier;
b) a peeler positioned to engage a base sheet and a lid sheet of a pocket which has been received in said opening station for peeling apart such a base sheet and lid sheet, to open such a pocket, said peeler including a lid driver for pulling apart a lid sheet and a base sheet of a pocket that has been received at said opening station;
c) an outlet, positioned to be in communication with an opened pocket through which a user can access a medicament dose from such an opened pocket;
d) an indexer for individually indexing the distinct pockets of the medicament carrier; and
e) a dose counter as described hereinbefore for counting each time a distinct medicament dose of the medicament carrier is indexed by said indexer.

Suitably, the indexer comprises a rotatable index wheel having recesses therein, said index wheel being engageable with a medicament carrier in use with said medicament dispenser such that said recesses each receive a respective pocket of the base sheet of a blister strip in use with said medicament dispenser.

Suitably, the rotatable index wheel additionally comprises a series of indentations located at its base and spaced in between the recesses.

Suitably, the indexer additionally comprises an interlock coupling to couple actuation of the dispenser to the index wheel. The interlock coupling reversibly locks the index wheel in place. Preferably, said interlock coupling comprises a foot portion having a toe and a heel, and a tail section. Preferably, said interlock coupling is pivotally mountable to the dispenser at its foot portion. Preferably, said toe fits into one of the indentations on the rotatable index wheel. Preferably, the interlock coupling is sprung to bias it towards location of the toe in one of the indentations.

Alternatively, the indexer comprises a gear and sprocket wherein teeth on the wheel fit into apertures or holes formed on one or both edges of a medicament carrier. The mechanism therefore resembles that of photographic film being advanced through a camera.

Alternatively, the indexer comprises an index ratchet which is moveable between a locked position whereby said ratchet engages a pocket on said medicament carrier and prevents further peeling thereof, and a release position allowing free movement of said medicament carrier. In this embodiment, actuation of said medicament dispenser actuates said lid driver and releases said index ratchet from a medicament carrier to allow peeling thereof.

Suitably, said lid driver comprises a wheel on which the lid sheet is wound up, said wheel having a winding surface which decreases in diameter when tension in the lid sheet increases. Preferably, said wheel comprises a plurality of resiliently flexible arms each extending therefrom at an angle with respect to a radius. The leading end of the lid sheet is looped over one of said resiliently flexible arms to secure the lid sheet to the wheel initially.

In one aspect, the lid driver comprise a mangle. The lid sheet passes through two rotating wheels which act as a mangle and is gripped at the point of contact with the wheels. The used portion of the lid sheet is collected in a chamber after it has passed through the mangle.

In another aspect, the lid driver comprise a roller. Preferably said roller is composed of a polymeric rubber and is positioned next to a guide wall. Preferably said roller has a smooth surface. Alternatively said roller has a knurled surface. The roller grips the lid sheet as it passes from the point at which it is separated from the base sheet through the space between the roller and the guide wall and the used portion of the lid sheet is then collected in a chamber. The roller has the advantage over the mangle described above in that a greater degree of contact between the roller wheel and the lid sheet occurs—the lid sheet is squeezed through the roller and may pass around about $1/3$ of the roller wheel. This provides a higher level of grip and pulling force than with a mangle. The force required to turn the roller is constant throughout the use of the device and does not vary according to how much of the lid sheet has been peeled away from the base sheet. This is in contrast to the wheel described above where the forces required to turn the wheel may vary due to the fact that the lid sheet is wound around the wheel. The lid sheet is not wound around the roller. The roller also has the advantage that the lid sheet does not have to be looped around or fixed to the roller before use of the device, therefore simplifying assembly of the device and reducing costs.

In a further aspect, the lid driver comprise a lid spool. The lid spool comprises a toothed wheel with a central upward cylindrical projection on which the lid sheet may be wound when it has been separated from the base sheet. The lid spool may have a mechanical gearing mechanism which is driven on actuation of the dispenser; the lid sheet is pulled away from the base sheet and wound onto the lid spool, causing the rotatable indexing wheel to turn and index the base sheet by one dose. An interlock coupling, as described supra, may be moved along the base of the rotatable indexing wheel until it fits into the next base recess. The positioning of the interlock coupling in this recess limits the movement of the lid spool to the distance between two pockets on the base sheet and therefore prevents the amount of lid sheet which is wound around the lid spool from increasing as the diameter of the lid spool is increased.

Suitably, said lid driver comprises a wheel on which the lid sheet is wound up. Typically, said lid sheet wheel has an effective winding surface, the diameter of which increases after every use of the dispenser as the lid sheet winds around the wheel.

In order to ensure that the same dose is dispensed every time, that is, only a defined number of medicament pocket are opened for every actuation of the dispenser, there may be provided an electronic control system comprising means to limit the extent of movement of said lid driver, in order to control the length of medicament carrier peeled by said peeler. Hence, the medicament carrier is indexed by the same amount each time and a uniform, consistent dose is always dispensed.

The dispenser may further comprise compensating means positioned between said opening station and said lid sheet wheel for reducing the length of said lid sheet therebetween to compensate for any increase in the diameter of the effective winding surface of the lid sheet wheel during use of the dispenser.

Typically, the compensating means takes the form of a flexible member. The flexible member may take the form of a flexible elongate arm about which the lid sheet is fed. The arm may flex inwards as tension in the lid sheet increases, and thus shorten the length of lid sheet between the opening station and the lid driver.

Suitably, the compensating means takes the form of a spring which reduces in length as tension increase in the lid sheet between the opening station and the lid driver. Typically a piston head is mounted on one end of the spring about which the lid sheet is fed. The other end of the spring may be fixed. As tension in the lid sheet increases the piston is driven down onto the spring.

Suitably, the compensating means takes the form of a sprung-loaded tensioner.

Suitably, the flexible member is resilient so that on removal of tension from the lid sheet, the flexible member will return to its rest position. Thus, the internal mechanism can be reloaded with a new medicament carrier after the used carrier is removed.

Alternatively, or in addition, the dispenser may comprise a clutch means to adjust for any increase in the diameter of the effective winding surface of the lid driver during use of the dispenser. In one aspect, the clutch means communicates with the indexer and the lid driver, and comprises a gearing surface defining plural gear engagement positions; and plural gear teeth for engaging said plural gear engagement positions, wherein the plural gear teeth are arranged such that at any one time only a single gear tooth engages a single gear engagement position.

It will be appreciated that, in use, the clutch means acts to compensate for the increase in diameter of said effective winding surface of the lid driver. The clutch means allows for slippage when the tension in the lid sheet is greater than the force required to peel apart the lid sheet and the base sheet.

It will be appreciated that in total, the clutch means effectively defines a number of individual gear positions which is greater than the number of gear engagement positions. This is therefore advantageous over a traditional slipping clutch arrangement comprising intermeshing gear wheels, where the effective number of individual gear positions defined is either equal to, or no more than, the number of gear engagement positions defined by one of the gear wheels. The clutch means herein is also typically more compact than traditional slipping clutch arrangements e.g. because it enables smaller gearing surfaces to be employed.

Suitably, the gearing surface and plural gear teeth are arranged such that the number of individual gear positions defined is equal to the number of gear engagement positions multiplied by the number of gear teeth. In one example, if the gearing surface defines 60 gear engagement positions and there are 6 gear teeth, then up to 360 individual gear positions are definable (e.g. 1° resolution on a rotating gear system).

Suitably, the gearing surface defines from 20 to 100, preferably from 40 to 80 gear engagement positions. Suitably, the number of gear teeth is from 2 to 20, preferably from 3 to 10.

In one aspect, the gear engagement positions are equally spaced (e.g. equidistantly spaced) and the gear teeth are offset (e.g. non-equidistantly spaced) relative thereto. Such offset arrangement maximises the number of effective individual gear positions which are capable of definition. An example of this aspect, is a Vernier spring arrangement.

In another aspect, the gear engagement positions are also equally spaced (e.g. equidistantly spaced) and the gear teeth are located on a wobbling element capable of wobbling the gear teeth to plural offset (e.g. non-equidistantly spaced) positions. Such a wobbling offset arrangement also maximises the number of effective individual gear positions which are capable of being defined. An example of this aspect, is the wobbling wheel arrangement described herein.

In aspects, the clutch means is non-integral with either of the lid driver or the indexer, but forms a separate interconnecting component.

Suitably, the gearing surface comprises a gear wheel. As used herein, the term gear wheel encompasses, for example, a wheel, spindle or spool.

Suitably, the gear teeth may be arranged to be in ratchet form (i.e. enabling movement in one direction only).

Suitably, the gearing surface and gear teeth are in biased (e.g. sprung) engagement.

In one aspect, the lid driver comprises a spiked wheel. As the spiked wheel turns, the lid sheet is pulled over it and the spikes perforate parts of the lid sheet to improve the grip on the lid sheet. The lid sheet then passes out into a chamber where it collects.

In another aspect, the lid driver comprises a clamp system. The clamp system comprises at least one angled spring which is pivotable at one end and grips the lid sheet at the other end. The clamp system is moved in the direction that the lid sheet is to be pulled and grips the lid sheet, pulling it and therefore peeling it away from the base sheet. The clamp system is then moved back to its rest position. This results in the spring pivoting and clamping the lid sheet, therefore preventing the lid sheet from being further peeled from the base sheet.

In another aspect, the used portion of the lid sheet may be passed around rollers and fed back onto the used portion of the base sheet after the medicament has been accessed to join back onto the base sheet. The lid sheet may be coated with a sticky substance to aid resealing. The use of this mechanism saves space as the used portions of the blister strip will be collected in the same area.

In another aspect, the coil comprising an unused medicament carrier (e.g. blister strip) may be surrounded by a constant force spring. Alternatively, the coil comprising the unused blister strip may be surrounded by an elastomeric band or band comprising a contractible material. The constant force spring, elastomeric band or band comprising a contractible material contracts as the coil reduces in size.

Suitably, said peeler additionally comprise a guide for guiding the lid sheet and base sheet along separate paths at the opening station. The lid sheet is passed around the guide portion onto the lid driver.

Alternatively, the guide comprises a roller mechanism. The lid sheet is fed over the rollers onto the lid driver.

Suitably, the internal mechanism additionally comprises a first chamber in which at least one strip is initially housed and from which it is dispensed and a second chamber to receive the used portion of the base sheet after it has been indexed around the index wheel and separated from the lid sheet.

Suitably, said first chamber and said second chamber are separated by a wall.

Suitably, said wall is movable to adjust the size of said first and second chambers.

In one aspect, the wall is pivotally mountable. Alternatively the wall is slidably mountable.

Suitably, the internal mechanism further comprises a third chamber to receive the used portion of the lid sheet and a fourth chamber which houses the index ratchet. The fourth chamber may communicate via a slit, which in turn extends upwardly within a mouthpiece and communicates with air inlets.

Suitably, the internal mechanism additionally comprises a crushing wheel to crush the medicament pockets after the medicament has been removed from them. The crushing wheel therefore reduces the space which the used portion of the base sheet takes up.

Typically, the internal mechanism for accessing said medicament contained within said medicament carrier is housed within a cassette.

Thus, in another embodiment, there is provided a medicament dispenser for dispensing medicament comprising: a body; a holder, shaped to fit within said body and movable relative to said body; and receivable by said holder, said cassette containing the medicament carrier.

Suitably, the medicament dispenser or cassette insert therefor comprises a mouthpiece.

The medicament dispenser may also be designed for nasal inhalation of a powdered medicament and may therefore incorporate a nosepiece as an alternative to a mouthpiece. If the medicament is in solid form, the dispenser may incorporate an exit channel for tablet release.

Suitably, the body covers the mouthpiece and an indexer (e.g. lever) when the cassette is in the non-dispensing position. This avoids the need for a separate cover and protects the mouthpiece from the ingress of dirt and contaminants during storage.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the electronic data management system is arranged to be responsive to or activated by the voice of a user. Thus, for example the system may be switched on or off in response to a voice command.

The electronic data management system may be integral with the body. Alternatively, the electronic data management system forms part of a base unit which is reversibly associable with the body.

Suitably, the medicament dispenser additionally comprises a data input system for user input of data to the electronic data management system. Preferably, the data input system comprises a man machine interface (MMI) preferably selected from a keypad, voice recognition interface, graphical user interface (GUI) or biometrics interface.

Energy may be conserved by a variety of means to enable the device to operate for longer on a given source of energy, such as a battery. Energy conservation or saving methods have additional advantages in terms of reducing the size requirements of the power source (e.g. battery) and thus the weight and portability of the medicament dispenser.

A variety of energy saving methods is available which generally involve reducing power consumption. One such method is to use a clock or timer circuit to switch the power on and off at regular or predetermined intervals. In another method the system can selectively switch on/off specific electronic devices, such as visual display units or sensors, in order to power these devices only when they are required to perform a particular sequence of events. Thus different electronic devices may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

Suitably, the system additionally comprises a visual display unit for display of data from the electronic data management system to the user. The display may for example, comprise a screen such as an LED or LCD screen. More preferably the visual display unit is associable with the body of the medicament dispenser.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement cassettes. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hard-wired link, an infrared link or any other suitable wireless communications link.

Suitably, the medicament dispenser additionally comprises an actuation detector for detecting actuation of the dispensing mechanism wherein said actuation detector transmits actuation data to the electronic data management system.

The medicament dispenser may additionally comprise a safety mechanism to prevent unintended multiple actuations of the dispensing mechanism. The patient is thereby protected from inadvertently receiving multiple doses of medicament in a situation where they take a number of short rapid breaths. More preferably, the safety mechanism imposes a time delay between successive actuations of the releaser. The time delay is typically of the order of from three to thirty seconds.

Suitably, the medicament dispenser additionally comprises a release detector for detecting release of medicament, wherein said release detector transmits release data to the electronic data management system.

Suitably, the medicament dispenser additionally comprises a shake detector for detecting shaking of the medicament container (e.g. prior to actuation of the dispensing mechanism), wherein said shake detector transmits shake data to the electronic data management system.

Suitably, any actuation detector, release detector, or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

Suitably, the medicament dispenser additionally comprises a breath trigger for triggering the dispensing mechanism, said breath trigger being actuable in response to a trigger signal from the electronic data management system. Preferably, the electronic data management system includes a predictive algorithm or look-up table for deriving from the breath data when to transmit the trigger signal. For example, a real-time analysis of the patient breath waveform may be made and the trigger point derived by reference to that analysed waveform.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from said dispensing mechanism. In one aspect, the selector is manually operable. In another aspect, the selector is operable in response to a signal from the transmitter on the electronic data management system.

Suitably, the medicament dispenser comprises in association with a body or housing thereof, a first transceiver for transmitting and receiving data and in association with the medicament container, a second transceiver for transmitting and receiving data, wherein data is transferable in two-way fashion from the first transceiver to the second transceiver. The data is preferably in digital form and suitable for transfer by electronic or optical means.

One advantage of embodiments of this type is the ability to store many types of information in different parts of the memory structure of the transceivers. The information is furthermore stored in a form which is readily and accurately transferable. The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

In the event that the supply of medicament within the container becomes exhausted, or that the shelf life of the medicament has expired, or that the first transceiver does not recognise the batch code on the second transceiver, activation of the dispenser may be prevented to safeguard the user. Activation may also be prevented if the medicament has been exposed to extreme environmental conditions for periods outwith the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the device. Or alternatively, data may be stored in a database memory of the electronic data management system and periodically downloaded to any transceiver. In either case, a history of the usage of the device may be built up in the memory of a transceiver.

In one embodiment herein, a history of the usage of the medicament dispenser is transferred to the second transceiver. When the medicament carriers in the cassette are exhausted it is exchanged by the patient for a new refill cassette. At the point of exchange, which will typically occur at the pharmacy, data may be transferred from the exhausted cassette to the refill and vice-versa. Additionally, usage history data may be read from the refill and transferred to a healthcare data management system for example comprising a network computer system under the control of a healthcare data manager.

Suitably, the first and second transceiver each comprise an antenna or equivalent for transmitting or receiving data and connecting thereto a memory. The memory will typically comprise an integrated circuit chip. Either transceiver may be configured to have a memory structure which allows for large amounts of information to be stored thereon. The memory structure can be arranged such that parts of the memory are read-only, being programmed during/after manufacture, other parts are read/write and further parts are password protectable. Initial transfer of information (e.g. on manufacture or on dispensing) to or from any transceiver can be arranged to be readily achievable by the use of a reader which is remote from the medicament dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell or kinetics-driven cell will be provided as required to any electronic component herein. The power source may be arranged to be rechargeable or reloadable.

Suitably, data is transferable in two-way fashion between the first and second transceiver without the need for direct physical contact therebetween. Preferably, data is transferable wirelessly between the first and second transceiver.

Suitably, the first transceiver is an active transceiver and the second transceiver is a passive transceiver. The term active is used to mean directly-powered and the term passive is used to mean indirectly-powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver.

Preferably, the reader will not need to be in direct contact with the tag or label to enable the tag or label to be read.

The tag may be used in combination and/or integrated with other traditional product labelling methods including visual text, machine-readable text, bar codes and dot codes.

Suitably, the integrated circuit chip has a read only memory area, a write only memory area, a read/write memory area or combinations thereof.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon. Suitably, any memory area is password protected.

Suitably, any memory area contains data in encrypted form. Electronic methods of checking identity, error detection and data transfer may also be employed.

In one aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

Suitably, the tag is on a carrier and the carrier is mountable on the body or holder of the medicament dispenser or on the cassette.

In one aspect, the carrier is a flexible label. In another aspect, the carrier is a rigid disc. In a further aspect, the carrier is a rectangular block. In a further aspect, the carrier is a collar ring suitable for mounting to the neck of an aerosol container. Other shapes of carrier are also envisaged.

Suitably, the carrier is mouldable or weldable to the cassette or housing. Suitably, the carrier encases the tag. More preferably, the carrier forms a hermetic seal for the tag.

In one aspect, the carrier comprises an insulating material such as a glass material or, a paper material or an organic polymeric material such as polypropylene. Alternatively, the carrier comprises a ferrite material.

The energy may be in any suitable form including ultrasonic, infrared, radiofrequency, magnetic, optical and laser form. Any suitable channels may be used to channel the energy including fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Suitably, the antenna of the RFID tag is capable of transmitting or receiving radiofrequency energy having a frequency of from 100 kHz to 2.5 GHz. Preferred operating frequencies are selected from 125 kHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a microelectronic memory chip and the first transceiver comprises a reader for said microelectronic memory chip. The microelectronic memory chip may comprise an Electrically Erasable Programmable Read Only Memory (EEPROM)

chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet which may in embodiments be capable of receiving printed text thereon.

In one aspect, the first transceiver is integral with the body such that a single unit is comprised. The first transceiver may for example be encased within or moulded to the body.

In another aspect, the first transceiver forms part of a base unit which is reversibly associable with the body. The base unit may for example, form a module receivable by the body such as a snap-in module.

Suitably, the medicament dispenser additionally comprises a communicator for wireless communication with a network computer system to enable transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be either a traditional copper wire system, a cellular system or an optical network.

In another aspect, the network computer system comprises a private access network computer system. The private access network system may for example, comprise an Intranet or Extranet which may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source can be made available thereto. More preferably, information from the user-specific network address can be made available to the remote information source.

In one aspect, the remote information source is a medicament prescriber, for example a doctors practice. Information transferred from the medicament prescriber may thus, comprise changes to prescription details, automatic prescription updates or training information. Information transferred to the medicament prescriber may comprise compliance information, that is to say information relating to the patient's compliance with a set prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

The dose counter herein is suitable for use with a medicament dispenser.

In one aspect, the dose counter is supplied as an assembly for insertion into a medicament dispenser. The 'drive' for the dose counter is typically coupled to the 'drive' for the advancement/release of dose within the medicament dispenser.

Suitably, the dose counter assembly is received by the housing of a medicament dispenser such that it may move (e.g. float) slightly therewithin to assist effective meshing of the geared components thereof with those of the medicament dispenser.

Other aspects and features of the invention are contained in the appended claims as well as in the description of exemplary embodiments of the invention made with reference to the accompanying drawings.

BRIEF DESCRIPTION OF THE DRAWINGS

The invention will now be described with reference to the accompanying drawings in which:

FIG. 10a to 10i show a sequence for assembling the second dose counter of FIG. 7 within the housing of a dry powder inhaler device;

FIG. 13a shows a plan view from above of the count wheels of the third dose counter of FIG. 12.

DETAILED DESCRIPTION OF THE DRAWINGS

Figure 1:
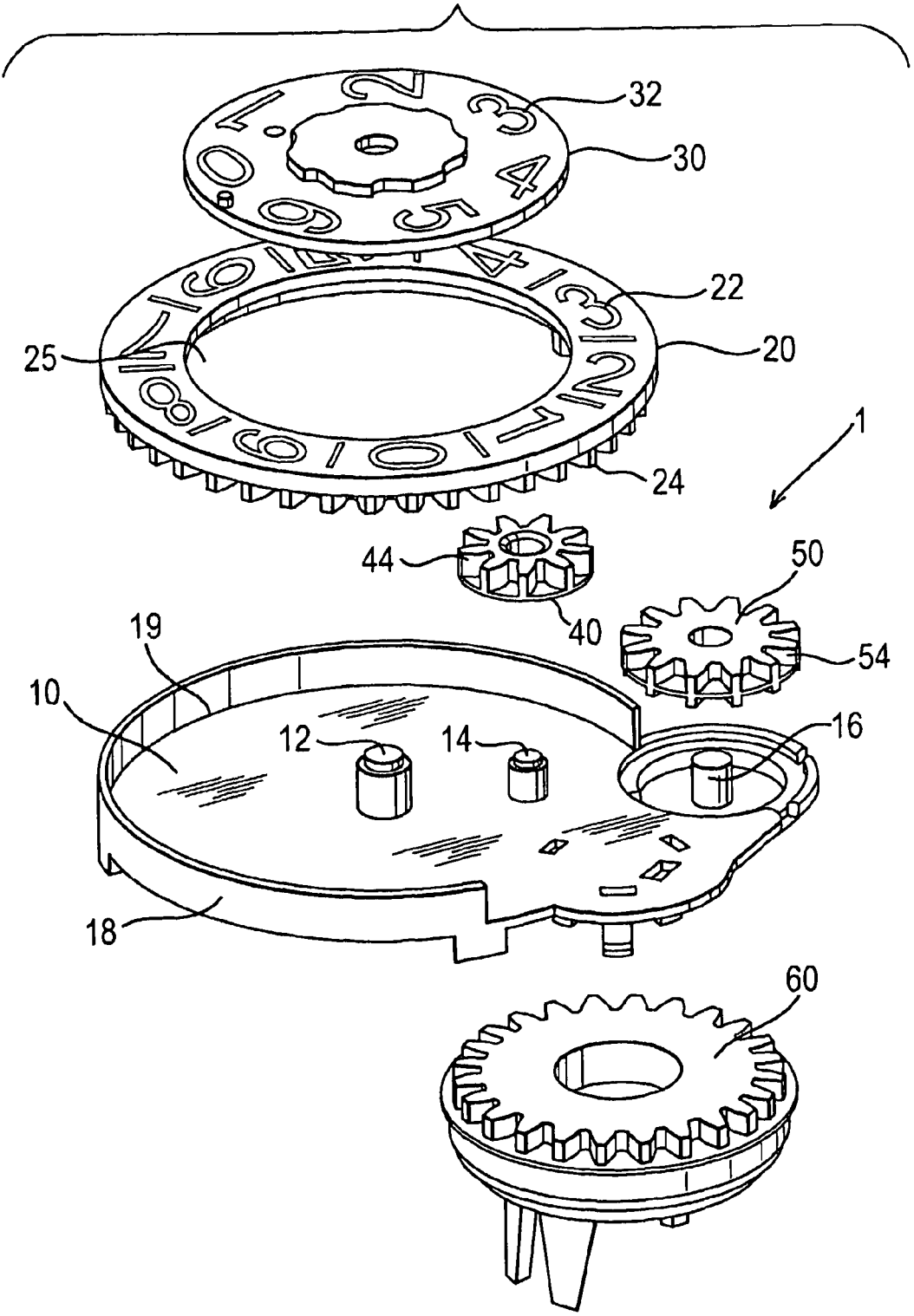
FIG. 1 shows an exploded view of a dose counter in accord with the present invention.
Figure 2:
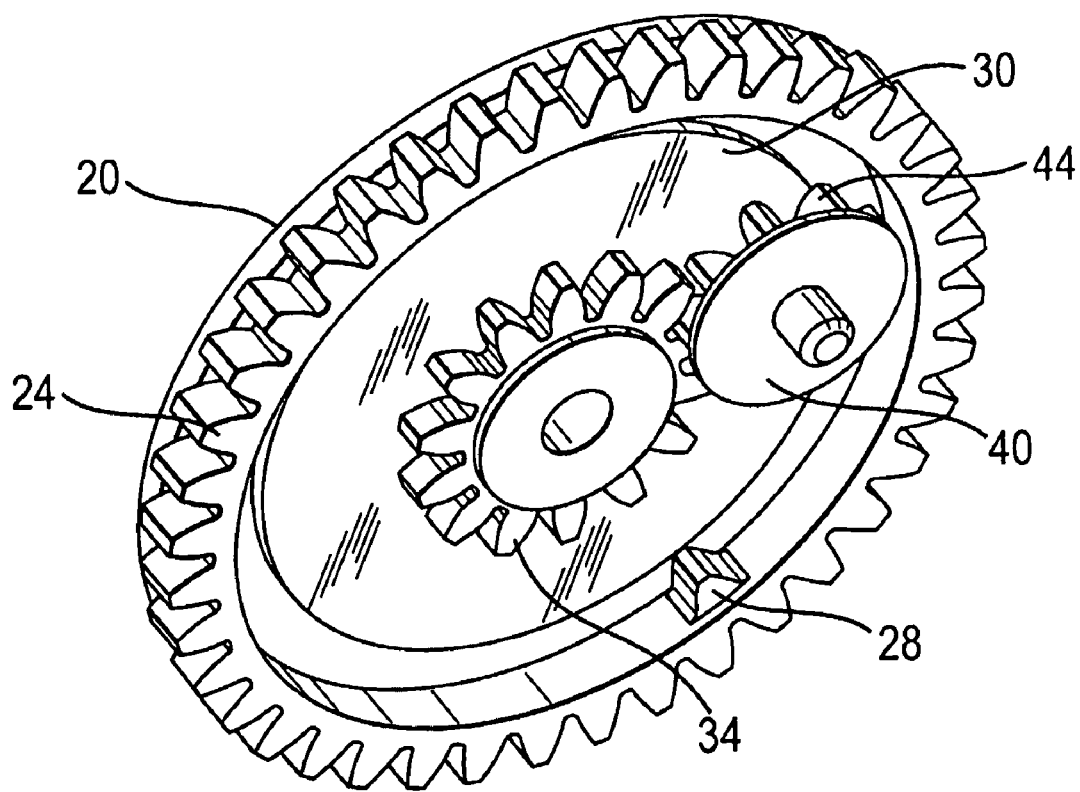
FIG. 2 shows a perspective view from the underside of part of the dose counter of FIG. 1.

FIG. 1 shows a dose counter assembly 1 herein and FIG. 2 shows the underside of the first 20 and second 30 count wheels and kick wheel 40 parts thereof.

The dose counter comprises a housing 10 provided with first 12, second 14 and third 16 spindle mountings, each capable of defining an axis of rotation and a circumferential wall 18 defining a circular retainer 19. First, ring-shaped count wheel 20 has 'units' count indicia 22 provided at spaced intervals on a top face thereof and a set of primary drive teeth 24 arranged circumferentially on the underside thereof. Second, circular form count wheel 30 also has 'tens of units' count indicia 32 provided at spaced intervals on a top face thereof and a set of secondary drive teeth 34 provided in annular arrangement to the underside thereof (only visible on FIG. 2). Kick wheel 40 has kick teeth 44 provided in annular arrangement at the top face thereof.

When assembled, first count wheel 20 is received for rotation within circular retainer and second count wheel 30 is received within the inner ring void 25 defined by ring-shaped first count wheel 20 and by first spindle 12. Thus, the first 20 and second 30 count wheels are in concentric relationship and both are rotatable about common axis of rotation defined in combination by the axis of first spindle 12 and the shape of the circular retainer 19. Kick wheel 40 is received by second spindle 14 for rotation thereabout (i.e. at a second axis of rotation defined by the second spindle 12 and therefore offset from the first axis of rotation). The set of kick teeth 44 of the kick wheel are in meshed relationship with the set of secondary drive teeth 34 of the second count wheel 30 such that rotary motion of the kick wheel 40 will result in rotary motion of the second count wheel 30. In turn, gear teeth 54 of step up gear wheel 50 (only visible on FIG. 1) mesh with the primary drive teeth 24 of the first count wheel 20 for drivable rotation of the first count wheel 20. The step up gear wheel 50 is in turn, drivable by index wheel 60 that is rotatable in response to user action e.g. in indexing a dose within a medicament dispenser (not shown). In an assembled medicament dispenser, index wheel 60 typically couples to a transport or drive mechanism (e.g. a drive gear) for advancing medicament dose to a use position.

First count wheel 20 may also be seen to be provided at its underside (see FIG. 2) with a fixed index tooth 28 arranged for intermittent meshing with the kick teeth 44 of the kick wheel 40 such that rotary motion of the kick wheel 40 results from rotary motion of the first count wheel 20 only when said intermittent meshing occurs.

In a first use operation, index wheel 60 is rotated in response to user action e.g. in indexing a dose within a medicament dispenser (not shown) thereby also causing step up gear wheel 50 to rotate. In turn, rotation of step up gear wheel 50 results in rotation of the first count wheel 20. The gearing of index wheel 60, step up gear wheel 50 and first count wheel 20 is arranged such that when a single dose is indexed by actuation of the index wheel 60, first count wheel 20 rotates by 36° such that a single indicium 22 thereon is advanced (i.e. the 'units' count moves on one unit).

Where the previous visible count was x9 (e.g. 09 or 19 or 29), the counting action resulting from the use operation is subtly different. Once again, index wheel 60 is rotated in response to user action causing step up gear wheel 50 to rotate and in rotation of the first count wheel 20 by 36° such that the 'unit' indicium 22 moves on from '9' to '0'. This rotation of the first count wheel 20 however, also brings the index tooth 28 into meshed relationship with the kick teeth 44 of kick wheel 40 such that the kick wheel 40 rotates and in turn, the second count wheel 30 rotates. As shown in FIG. 1, the gearing of the relevant wheels 20, 30, 40 is arranged such that the second count wheel 30 rotates by 360/7° (that is to say by 360/n° wherein n is the number of number spacings, where in this case n=7) such that a single indicium 32 thereon is advanced (i.e. the 'tens' count moves on exactly one unit).

It will be appreciated that the above usage has been described in terms of a counter 1 assembly arranged to count upwards (i.e. to count on from 'n' to 'n+1' on indexing), but that the counter assembly may be straightforwardly modified to count downwards (i.e. instead to count on from 'n' to 'n−1' on indexing).

Figure 3:
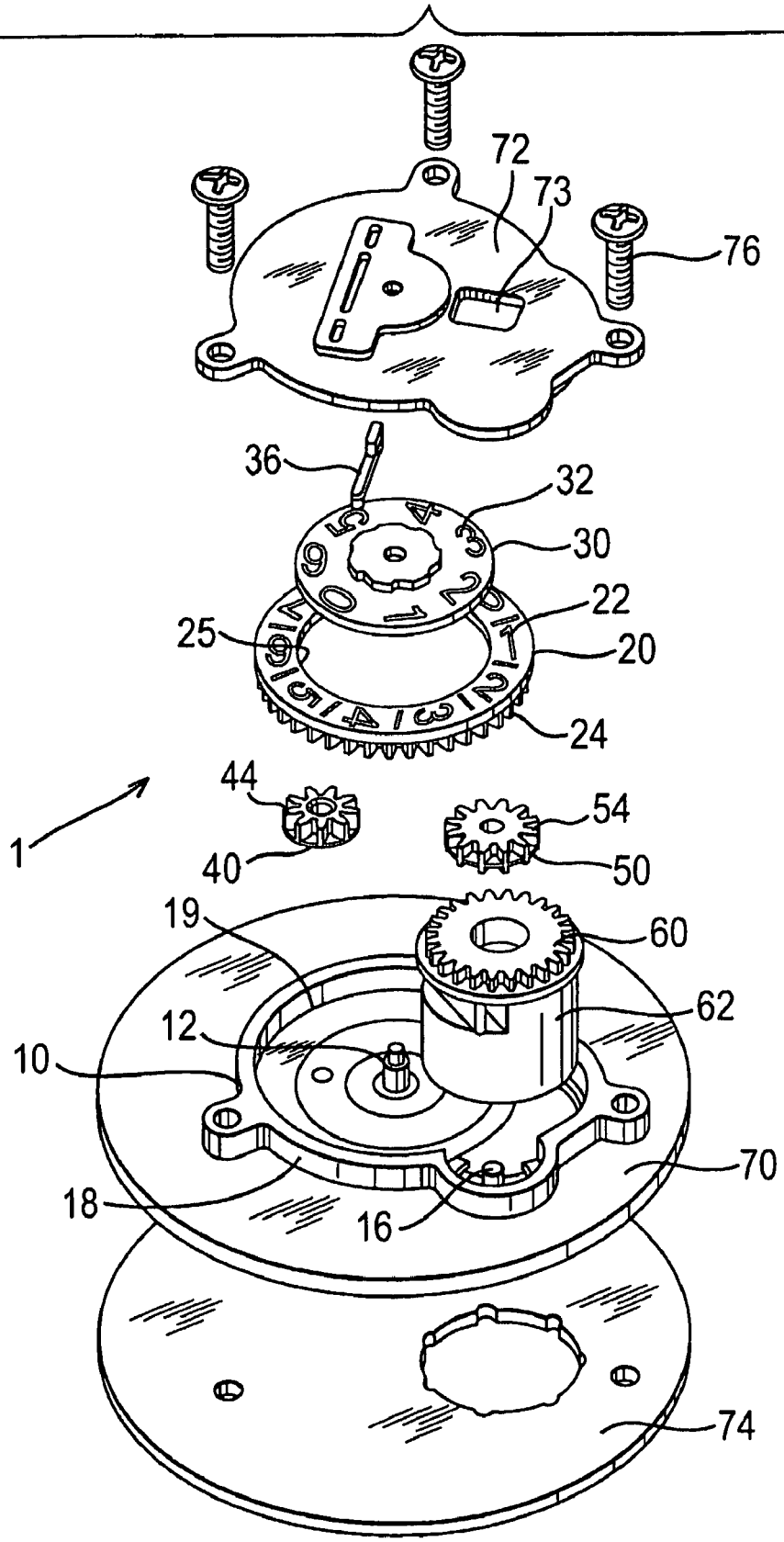
FIG. 3 shows an exploded view of a first medicament dispenser part assembly incorporating the dose counter of FIG. 1.

FIG. 3 shows a first medicament dispenser part assembly including the dose counter 1 of FIG. 1. The part assembly is suitably incorporated as part of a medicament dispenser suitable for the dispensing of medicament from individual blisters of an elongate, blister form medicament carrier.

The medicament dispenser assembly comprises the dose counter 1 of FIG. 1 comprising housing 10 provided with first 12, second (not visible) and third 16 spindle mountings, each capable of defining an axis of rotation and a circumferential wall 18 defining a circular retainer 19. First, ring-shaped count wheel 20 has 'units' count indicia 22 provided at spaced intervals on a top face thereof and a set of primary drive teeth 24 arranged circumferentially on the underside thereof. Second, circular form count wheel 30 also has 'tens of units' count indicia 32 provided at spaced intervals on a top face thereof and a set of secondary drive teeth provided in annular arrangement to the underside thereof (not visible). Kick wheel 40 has kick teeth 44 provided in annular arrangement at the top face thereof.

In the part assembly, housing 10 is mounted on chassis 70 and enclosed by outer housing comprising top cover 72 and bottom cover 74, which are held together by screws 76. The top cover 72 is provided with viewing window 73 through which indicia 22, 32 on first and second 20,30 count wheels are visible to show the 'current dose count'. The dose counter 1 is also provided at the second count wheel 30 with the additional feature of non-return arm 36, which simply functions to prevent reverse rotation thereof.

When assembled, first count wheel 20 is received for rotation within circular retainer and second count wheel 30 is received within the inner ring void 25 defined by ring-shaped first count wheel 20 and by first spindle 12. Thus, the first 20 and second 30 count wheels are in concentric relationship and both are rotatable about common axis of rotation defined in combination by the axis of first spindle 12 and the shape of the circular retainer 19. Kick wheel 40 is received by second spindle 14 for rotation thereabout (i.e. at a second axis of rotation defined by the second spindle 12 and therefore offset from the first axis of rotation). The set of kick teeth 44 of the kick wheel are in meshed relationship with the set of secondary drive teeth of the second count wheel 30 such that rotary motion of the kick wheel 40 will result in rotary motion of the second count wheel 30. In turn, gear teeth 54 of step up gear wheel 50 (only visible on FIG. 1) mesh with the primary drive teeth 24 of the first count wheel 20 for drivable rotation of the first count wheel 20. The step up gear wheel 50 is in turn, drivable by index wheel 60 that is rotatable in response to user action. It may also be seen that index wheel 60 is mounted to hub 62. In the medicament dispenser as a whole, the hub 62 receives the leading end of an elongate form blister strip (not shown) for pulling the blister strip through the medicament dispenser and individually indexing blisters containing medicament dose for dispensing thereof.

The mode of usage of the part assembly of FIG. 3 closely follows that of those use operations already described for the dose counter of FIGS. 1 and 2. It may be appreciated that, in the first step of a typical usage operation, rotation of the index wheel 60 arises as a result of hub 62 rotation as the blister strip is indexed by an indexing operation within the medicament dispenser.

Figure 4:
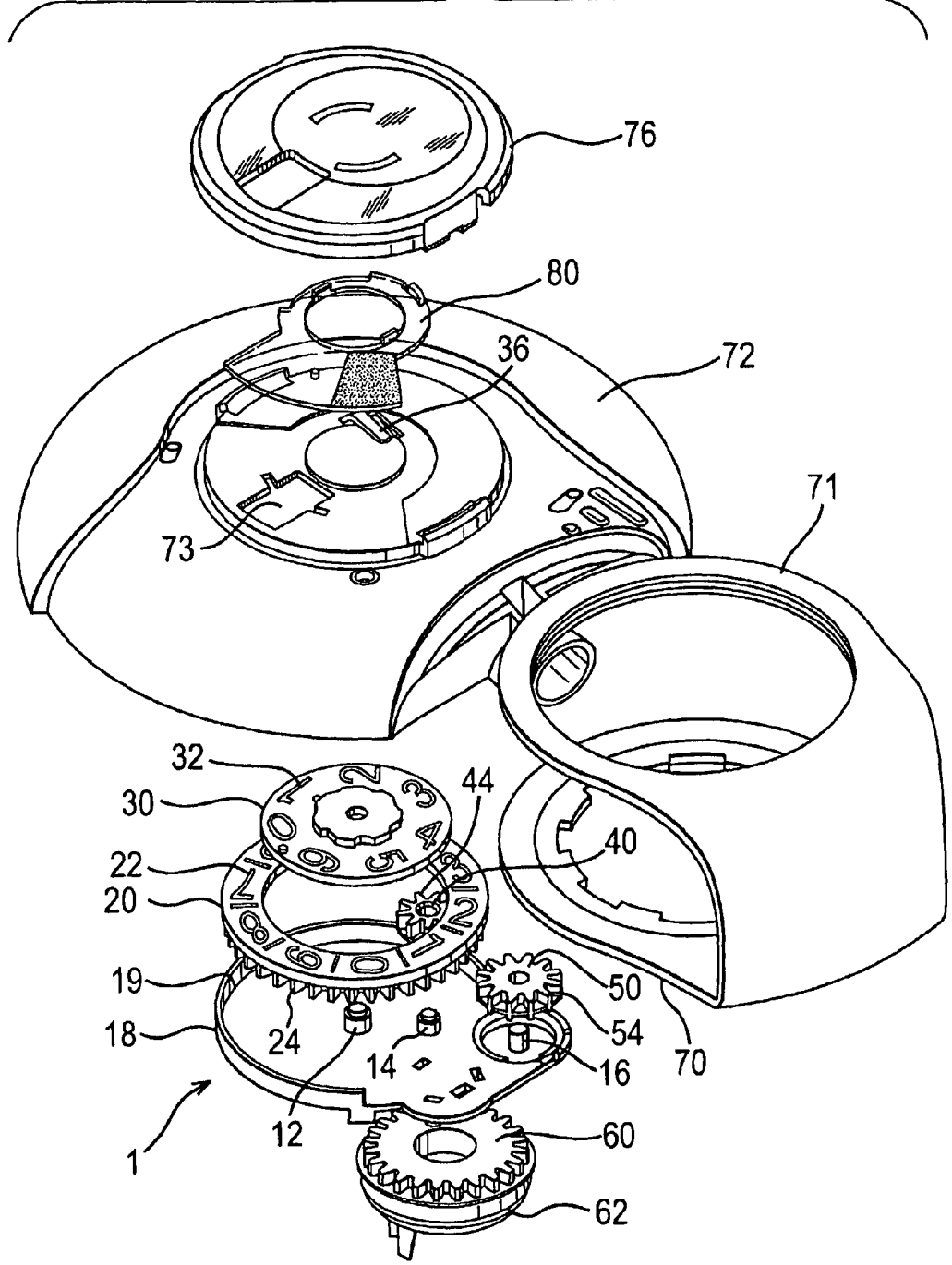
FIG. 4 shows an exploded view of a second medicament dispenser part assembly incorporating the dose counter of FIG. 1.

FIG. 4 shows a second medicament dispenser part assembly including the dose counter 1 of FIG. 1. The part assembly is suitably incorporated as part of a medicament dispenser suitable for the dispensing of medicament from individual blisters of an elongate, blister form medicament carrier.

The medicament dispenser assembly comprises the dose counter 1 of FIG. 1 comprising housing 10 provided with first 12, second 14 and third 16 spindle mountings, each capable of defining an axis of rotation and a circumferential wall 18 defining a circular retainer 19. First, ring-shaped count wheel 20 has 'units' count indicia 22 provided at spaced intervals on a top face thereof and a set of primary drive teeth 24 arranged circumferentially on the underside thereof. Second, circular form count wheel 30 also has 'tens of units' count indicia 32 provided at spaced intervals on a top face thereof and a set of secondary drive teeth provided in annular arrangement to the underside thereof (not visible). Kick wheel 40 has kick teeth 44 provided in annular arrangement at the top face thereof.

In the part assembly, housing 10 is mounted on chassis 70 having top element 71 and enclosed by outer housing comprising top cover 72 and bottom cover (not shown). The top cover 72 is provided with viewing window 73 through which indicia 22, 32 on first and second 20,30 count wheels are normally visible to show the 'current counts'. Shutter 80 is provided for selectively closing off the viewing window 73. More detail relating to the action of a suitable shutter 80 mechanism is provided at FIG. 5 and description thereof. Bezel 76 retains the shutter 80 to the top cover 72. The top cover 72 is also provided with a ratchet arm 36, which functions to prevent reverse rotation thereof. More detail relating to the action of ratchet arm 36 is provided at FIG. 6 and description thereof.

When assembled, first count wheel 20 is received for rotation within circular retainer and second count wheel 30 is received within the inner ring void 25 defined by ring-shaped first count wheel 20 and by first spindle 12. Thus, the first 20 and second 30 count wheels are in concentric relationship and both are rotatable about common axis of rotation defined in combination by the axis of first spindle 12 and the shape of the circular retainer 19. Kick wheel 40 is received by second spindle 14 for rotation thereabout (i.e. at a second axis of rotation defined by the second spindle 12 and therefore offset from the first axis of rotation). The set of kick teeth 44 of the kick wheel are in meshed relationship with the set of secondary drive teeth of the second count wheel 30 such that rotary motion of the kick wheel 40 will result in rotary motion of the second count wheel 30. In turn, gear teeth 54 of step up gear wheel 50 (only visible on FIG. 1) mesh with the primary drive teeth 24 of the first count wheel 20 for drivable rotation of the first count wheel 20. The step up gear wheel 50 is in turn, drivable by index wheel 60 that is rotatable in response to user action. As in FIG. 3, the index wheel 60 may itself be mounted to hub 62 such that in the medicament dispenser as a whole, the hub 62 receives the leading end of an elongate form blister strip (not shown) for pulling the blister strip through the medicament dispenser and individually indexing blisters containing medicament dose for dispensing thereof.

Usage operations of the part assembly of FIG. 4 closely follow those already described for the dose counter of FIGS. 1 and 2. It may be appreciated that, in the first step of such operations, rotation of the index wheel 60 may be configured to arise as with the part assembly of FIG. 3 as a result of hub 62 rotation as a blister strip is indexed by an indexing operation within the medicament dispenser.

Figure 5:
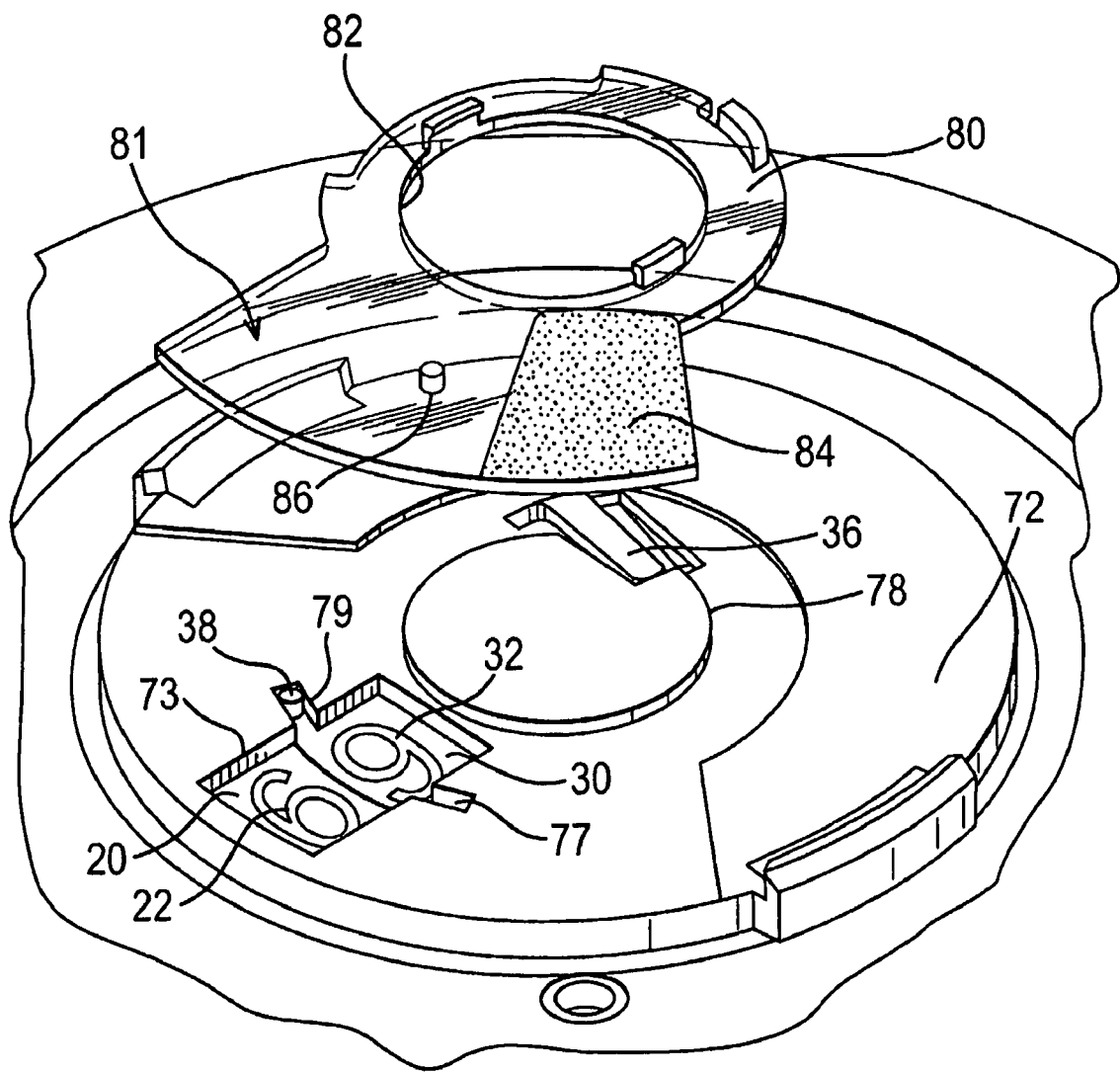
FIG. 5 shows a part exploded, detailed view of the shutter assembly of the second medicament dispenser part assembly of FIG. 4.

FIG. 5 shows a detailed view of the shutter assembly 80 for use with the second medicament dispenser part assembly of FIG. 4.

In more detail, top cover 72 is provided with viewing window 73 through which indicia 22, 32 on first 20 and second 30 count wheels are normally visible to show the 'current dose count'. Shutter 80 is also provided for selectively closing off the viewing window 73, as will now be described.

Shutter 80 has inner cut out ring portion 82 sized for receipt by circular mounting 78 about which the shutter 80 may rotate. The shutter 80 is formed of transparent material, but is also provided with printed blocking portion 84. The underside of the shutter 80 is provided with a protruding dog 86, which at the 'start of life' protrudes into first, cut out nick 77 and at the 'end of life' (as shown in FIG. 5) protrudes into second, cut out nick 79, wherein both nicks 77, 79 are provided to top cover 72 and locate just above the position of second ('tens of units') count wheel 30. That second count wheel is provided with drive projection 38 located as shown, between the number 6 and number 0 printed thereon.

Action of the shutter 80 is now described in relation to a dose counter that is arranged to 'count down' (in this case from '60' to '00'). During the count down from '60' to '00' the shutter is arranged such that dog 86 locates in first nick 77 and the indicia 22, 32 on both count wheels 20,30 is visible through the transparent shutter 80 body and viewing window 73. On moving from count '00' to (what would be) count '69' dog 86 on shutter 80 is engaged by drive protrusion 38 on the 'tens of units' count wheel 30 thereby causing the shutter 80 to be rotated (clockwise, as shown) to drag the printed portion 84 thereof over the viewing window 73, which is thereby blocked off. This corresponds to the 'end of life' point where the count is no longer visible.

The dog 86 may be adapted to lock the second count wheel 30 against further rotation when the shutter 80 is closed by preventing the drive protrusion 38 from passing by it. This also locks the kick wheel 40 in place and prevents the first count wheel 20 from further rotation when the index tooth 28 meshes with the kick teeth 44 at the end of the next revolution of the first count wheel 20 around the second count wheel 30.

In variations, the shutter 80 may be sprung to prevent undesirable reverse movement thereof e.g. to again reveal the indicia 22, 32 below the viewing window 73 after the 'end of life' point has been reached.

As an alternative or addition to the shutter 80, it is possible to have the protrusion 38 on the second counter wheel 30 run in a channel in the top cover 72. When the indicium 32 on the second counter wheel reaches '0' the protrusion 38 reaches the end of the channel, thereby preventing it from turning any further. This also locks the kick wheel 40 in place and prevents the first counter wheel 20 from advancing as the index tooth 28 attempts to drive the kick wheel 40. In this embodiment, and the other lock-out embodiment described above, the top of the index wheel 60 would be split into two components with one section driven by the lower index wheel and a friction drive to a separate gear mounted on top. As the count wheels 20, 30 lock, the gear on top of the index wheel 60 would slip thereby permitting the blister strip to advance in the medicament dispenser but not allowing the count to change. Alternatively, the lock-out of the dose counter 1 may prevent further operation of the medicament dispenser by locking its operating mechanism.

Figure 6:
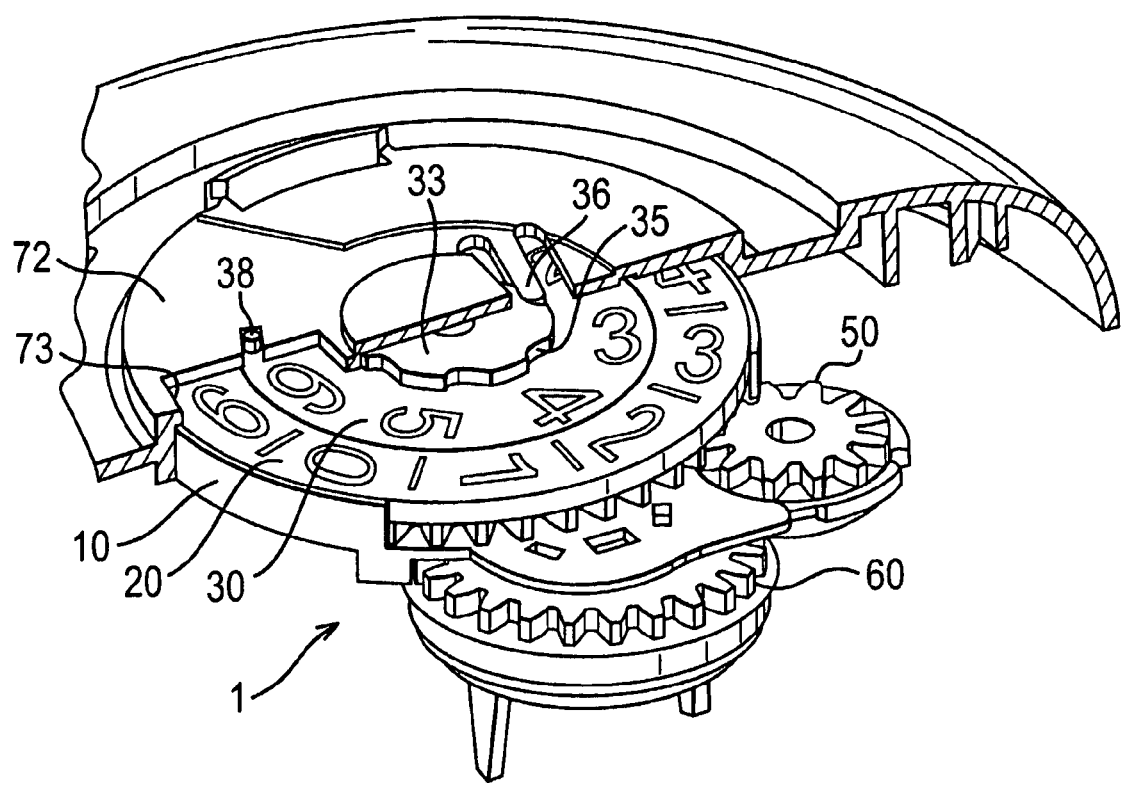
FIG. 6 shows a cut away, detailed view of a ratchet arm assembly of the second medicament dispenser part assembly of FIG. 4.

FIG. 6 shows a cut away, detailed view of a ratchet arm assembly suitable for use with the second medicament dispenser part assembly of FIG. 4.

In more detail, dose counter 1 comprises housing 10 for housing concentrically arranged first 20 and second 30 count wheels, each having count indicia 22, 32 provided at spaced intervals on a top face thereof. Kick wheel 40 and index wheel 60 are also visible in FIG. 6. Housing 10 mates with top cover 72, which is provided with viewing window 73 through which indicia 22, 32 on first and second 20,30 count wheels are normally visible to show the 'current count'.

The top cover 72 is also provided with a ratchet arm 36, which engages cam profile 35 of flared star element 33 provided to the top face of second ('tens of units') count wheel 30. The cam profile 33 (which in effect, acts as pawl to the ratchet arm 36) acts in combination with the ratchet arm 36 such as to ensure correct alignment of the indicia 22, 32 and also to prevent reverse rotation of the second count wheel 30 as a result e.g. of patient tampering or due to the effects of undesirable vibration or impact.

Figure 6A:
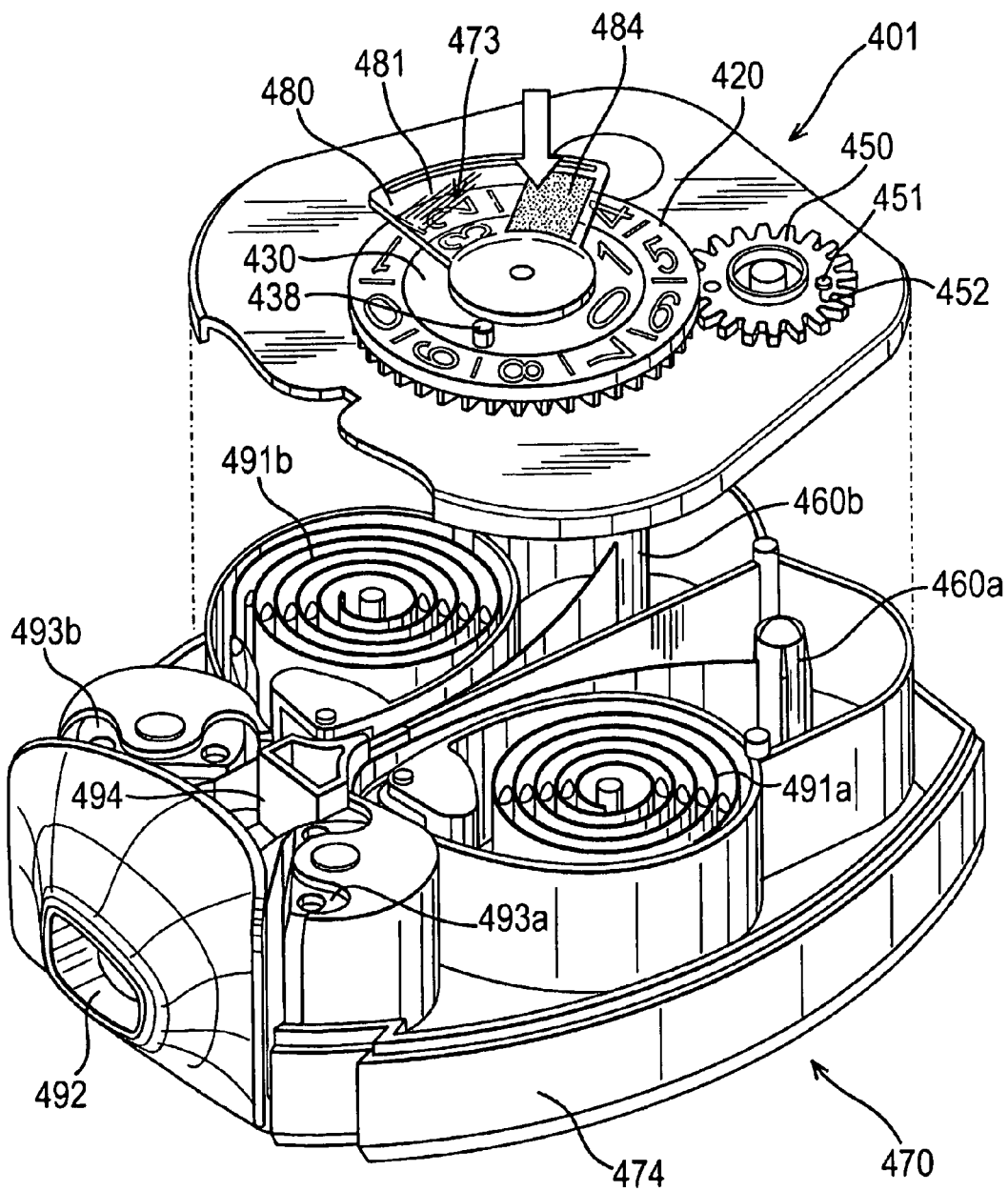
FIG. 6a shows a perspective, part-exploded view of a dry powder inhaler incorporating an assembly comprising a dose counter according to the present invention.

FIG. 6a shows a medicament dispenser 470 which incorporates a dose counter 401 which is a modified version of the dose counter 1 of FIGS. 4 to 6 with like features being assigned like numerals (as elsewhere in the description of the drawings). Thus, the dose counter 401 operates in like manner to the dose counter 1 of FIGS. 4 to 6, including operating in the same way to move the shutter 480 from a viewing position, in which the count indicia of the count wheels 420, 430 in the viewing window 473 of the medicament dispenser 470 are visible through the see-through portion 481 of the shutter 480, to a shuttering position, in which the non-see-through portion 484 (printed, opaque etc.) of the shutter 480 shutters the viewing window 473.

In more detail, the medicament dispenser 470 as shown in FIG. 6a comprises a bottom cover 474 holding first and second elongate, peelable blister strips 491a, 491b, each defining a series of blisters, each containing individual doses of inhalable medicament in dry powder form. The strips 491a, 491b are movable within the bottom cover 474 by means of first and second drive hubs 493a, 493b, respectively, that allow for sequential opening (i.e. by peeling off action) of each blister to allow the contents thereof to be made available at manifold 494 for inhalation by a patient at mouthpiece 492.

In turn, first drive hub 493a is in coupled relationship (e.g. via complex gear train, not shown) with a first base take-up drive 460a such that drivable rotation of first drive hub 493a results in rotation of the base take-up drive 460a, thereby resulting in both advancement of the first blister strip 491a, as described above, and advancement of the counter 401 via drive wheel 450 and its interaction with base take-up drive 460a and the count mechanism.

The second drive hub 493a is also in coupled relationship with a second base take-up drive 460b such that drivable rotation of the second drive hub 493b results in rotation of the second base take-up drive 460b and advancement of the second blister strip 491b.

In yet more detail, the base spool drives 460a, 460b both rotate in response to user actuation of the medicament dispenser to advance a medicament dose from the first and second blister strips 491a, 491b to a use position at which the medicament doses, for instance being doses of different medicaments, are inhaled by the user inhaling at the mouthpiece 492.

The rotation of the base spool take-up drive 460a of the medicament dispenser 470 drives rotation of the drive wheel 450. This in turn results in rotation of one, or both, of the count wheels 420, 430, depending on where the dose counter 401 is in its count sequence, as previously described with reference to FIGS. 4 to 6. So, the dose counter display is updated to reflect the advancement of the medicament doses from each strip 491a, 491b to the use position (and subsequent simultaneous or sequential inhalation by the patient through the mouthpiece 492). In other words, the "dose" for the purposes of the "dose count" recorded by the dose counter 401 in this instance means a combined dose from each strip 491a, 491b.

The counter sub-assembly 401 is provided with a locking pin 451, which protrudes through an aperture 452 of the drive wheel 450 and an aperture (not shown) of the base plate 410 to lock the drive wheel 450, thereby preventing any counts being recorded during transit of the counter sub-assembly 401. In a typical manufacturing operation, the sub-assembly 401 is therefore assembled and locking pin 451 inserted to lock drive wheel 450. The locked sub-assembly 401 is then transported for loading into the medicament dispenser 470 for use therewith. After loading, the locking pin 451 is removed such that the drive wheel 450 is now responsive to the base take-up drive 460.

Figure 7:
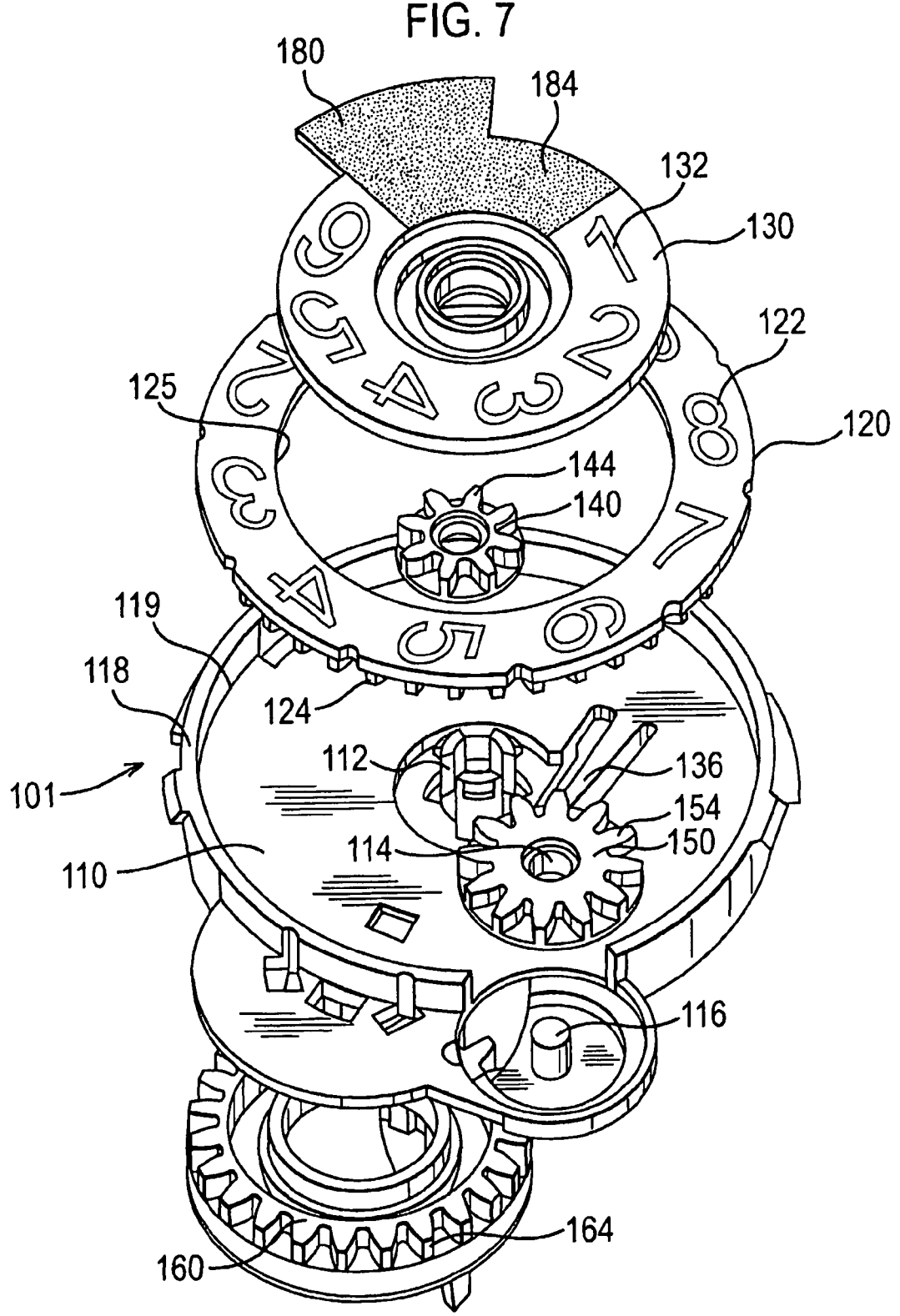
FIG. 7 shows an exploded view of a second dose counter in accord with the present invention.
Figure 8:
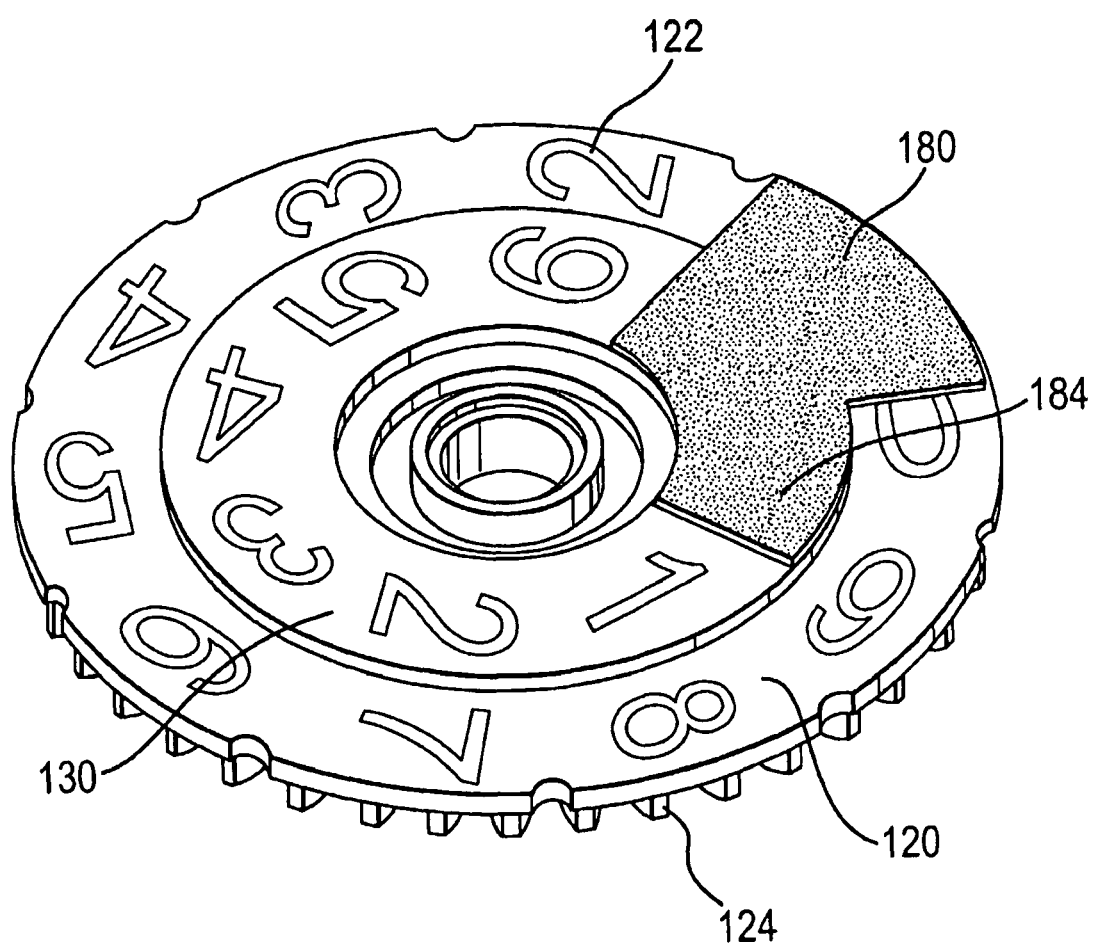
FIG. 8 shows a view from above of the first and second counter wheels of the second dose counter of FIG. 7.
Figure 9:
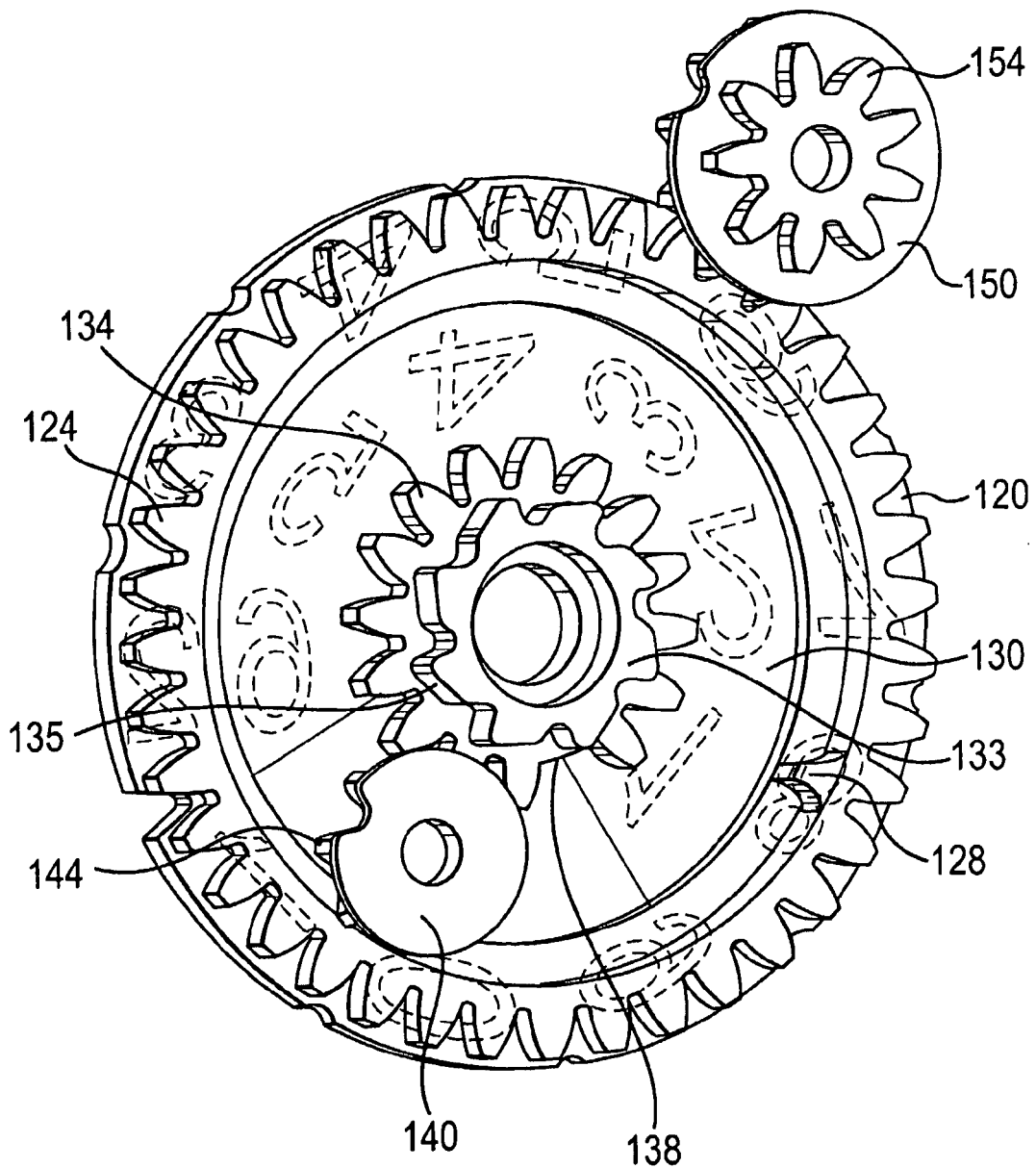
FIG. 9 shows a perspective view from the underside of part of the second dose counter of FIG. 7.

FIG. 7 shows a second dose counter assembly 101 herein; FIG. 8 shows a top view of the first 120 and second 130 count wheel parts thereof; and FIG. 9 shows the underside of the first 120 and second 130 count wheels and kick wheel 140 parts thereof. It may be appreciated that the second dose counter assembly is a variation of that shown in FIGS. 1 and 2.

The dose counter comprises a housing 110 provided with first 112, second 114 and third 116 spindle mountings, each capable of defining an axis of rotation and a circumferential wall 118 defining a circular retainer 119. First, ring-shaped count wheel 120 has 'units' count indicia 122 provided at spaced intervals on a top face thereof and a set of primary drive teeth 124 arranged circumferentially on the underside thereof. Second, circular form count wheel 130 also has 'tens of units' count indicia 132 provided at spaced intervals on a top face thereof and a set of secondary drive teeth 134 provided in annular arrangement to the underside thereof (only visible on FIG. 9). It may be noted that at stop position 138, one of the secondary drive teeth 134 has been removed. The reason for this will become clear from the later description. The second count wheel 130 is also provided with coloured portion 184 and protruding shutter 180, which in this embodiment is of the same colour as the coloured portion, for instance red. Kick wheel 140 has kick teeth 144 provided in annular arrangement at the top face thereof.

When assembled, first count wheel 120 is received for rotation within circular retainer and second count wheel 130 is received within the inner ring void 125 defined by ring-shaped first count wheel 120 and by first spindle 112 such that clearance exists between the first 120 and second 130 count wheels. Thus, the first 120 and second 130 count wheels are in concentric relationship with the level of the second count wheel 130 slightly raised relative to that of the first count wheel 120 to enable shutter 180 to protrude over and above the first count wheel 120. Both wheels 120, 130 are rotatable about a common axis of rotation defined in combination by the axis of first spindle 112 and the shape of the circular retainer 119. Kick wheel 140 is received by second spindle 114 for rotation thereabout (i.e. at a second axis of rotation defined by the second spindle 114 and therefore offset from the first axis of rotation). The set of kick teeth 144 of the kick wheel are in meshed relationship with the set of secondary drive teeth 134 of the second count wheel 130 such that rotary motion of the kick wheel 140 results in rotary motion of the second count wheel 130. In turn, gear teeth 154 of step up gear wheel 150 (only visible on FIGS. 7 and 9) mesh with the primary drive teeth 124 of the first count wheel 120 for drivable rotation of the first count wheel 120. The step up gear wheel 150 is in turn, drivable by index wheel 160 having teeth 164 that is rotatable in response to user action e.g. in indexing a dose within a medicament dispenser (not shown). In an assembled medicament dispenser, index wheel 160 typically couples to a transport or drive mechanism (e.g. a drive gear) for advancing medicament dose to a use position.

First count wheel 120 may also be seen to be provided at its underside (see FIG. 9) with a fixed index tooth 128 arranged for intermittent meshing with the kick teeth 144 of the kick wheel 140 such that rotary motion of the kick wheel 140 results from rotary motion of the first count wheel 120 only when said intermittent meshing occurs.

The housing 110 may also be seen to be provided with a ratchet arm 136, which engages cam profile 135 of flared star element 133 (see FIG. 9) provided to the underside of second ('tens of units') count wheel 130. The cam profile 133 (which in effect, acts as pawl to the ratchet arm 136) acts in combination with the ratchet arm 136 such as to ensure correct alignment of the indicia 122, 132 and also to prevent reverse rotation of the second count wheel 130 as a result e.g. of patient tampering or due to the effects of undesirable vibration or impact.

In a subtle aspect, it may be seen that the profile of all teeth 124, 134, 144, 154, 164 has a flanged form, which is selected to optimise the various toothed engagements necessary for effective gearing and inter-operability of the wheels 120, 130, 140, 150, 160 of the counter.

As shown, the second counter 101 is arranged to count down. Thus, in a first use operation, index wheel 160 is rotated in response to user action e.g. in indexing a dose within a medicament dispenser (not shown) thereby also causing step up gear wheel 150 to rotate. In turn, rotation of step up gear wheel 150 results in rotation of the first count wheel 120. The gearing of index wheel 160, step up gear wheel 150 and first count wheel 120 is arranged such that when a single dose is indexed by actuation of the index wheel 160, first count wheel 120 rotates by 36° such that a single indicium 122 thereon is advanced (i.e. the 'units' count moves down one unit).

Where the previous visible count was x0 (e.g. 40 or 30 or 20), the counting action resulting from the use operation is subtly different. Once again, index wheel 160 is rotated in response to user action causing step up gear wheel 150 to rotate and in rotation of the first count wheel 120 by 36° such that the 'unit' indicium 122 moves on from '0' to '9'. This rotation of the first count wheel 120 however, also brings the index tooth 128 into meshed relationship with the kick teeth 144 of kick wheel 140 such that the kick wheel 140 rotates and in turn, the second count wheel 130 rotates. As shown in FIG. 7, the gearing of the relevant wheels 120, 130, 140 is arranged such that the second count wheel 130 rotates by 360/8° (that is to say by 360/n° wherein n is the number of number spacings, where in this case n=8 because there are six indicia 132; one coloured portion 184; and one shutter portion 180) such that a single indicium 132 thereon is advanced (i.e. the 'tens' count moves down exactly one unit).

Where the previous visible count was 10 (i.e. x=1), the counting action resulting from the use operation is again subtly different in that the kick wheel 140 action, as described above, results in the coloured (e.g. red) portion 184 of the second count wheel 130 being advanced into place such that the next display is 'red 9' (i.e. coloured portion 184; and indicia 122 is number 9).

Where the previous visible count was 'red 0' (i.e. x=0), the counting action resulting from the use operation is still again subtly different in that the kick wheel 140 action, as described above, results in the shutter portion 180 of the second count wheel 130 being advanced into place such that the next display is fully shuttered off (i.e. no indicia 122, 132 visible at all). Additionally, the stop position 138 in the set of secondary drive teeth 134 is brought into opposed relation with the kick teeth 144 whereby the kick teeth 144 and the secondary drive teeth 134 no longer mesh. Thus, if the first count wheel 120 continues to rotate, e.g. in response to continued user operation of a medicament dispenser into which the dose counter 101 is incorporated, notwithstanding that all medicament doses have been dispensed, the index tooth 128 of the first count wheel 120 will still intermittently mesh with the kick teeth 144 to cause the kick wheel 140 to rotate. However, this rotation of the kick wheel 140 will not be transmitted to the second count wheel 130, due to the stop position 138, and the shutter 180 remains in the shuttering position.

It will be appreciated that the above usage of the second counter has been described in terms of a counter assembly 101 arranged to count downwards (i.e. to count on from 'n+1' to 'n' on indexing), but that the counter assembly may be straightforwardly modified to count upwards (i.e. instead to count on from 'n' to 'n+1' on indexing).

In this embodiment of the invention, the second count wheel 130 is integrally formed with the shutter portion 180.

FIGS. 10*a* to 10*i* show a sequence for assembling the second dose counter of FIG. 7 within the housing of a dry powder inhaler device. For simplicity, only the parts involved in each assembly step are labelled on each relevant Figure.

Figure 10A:
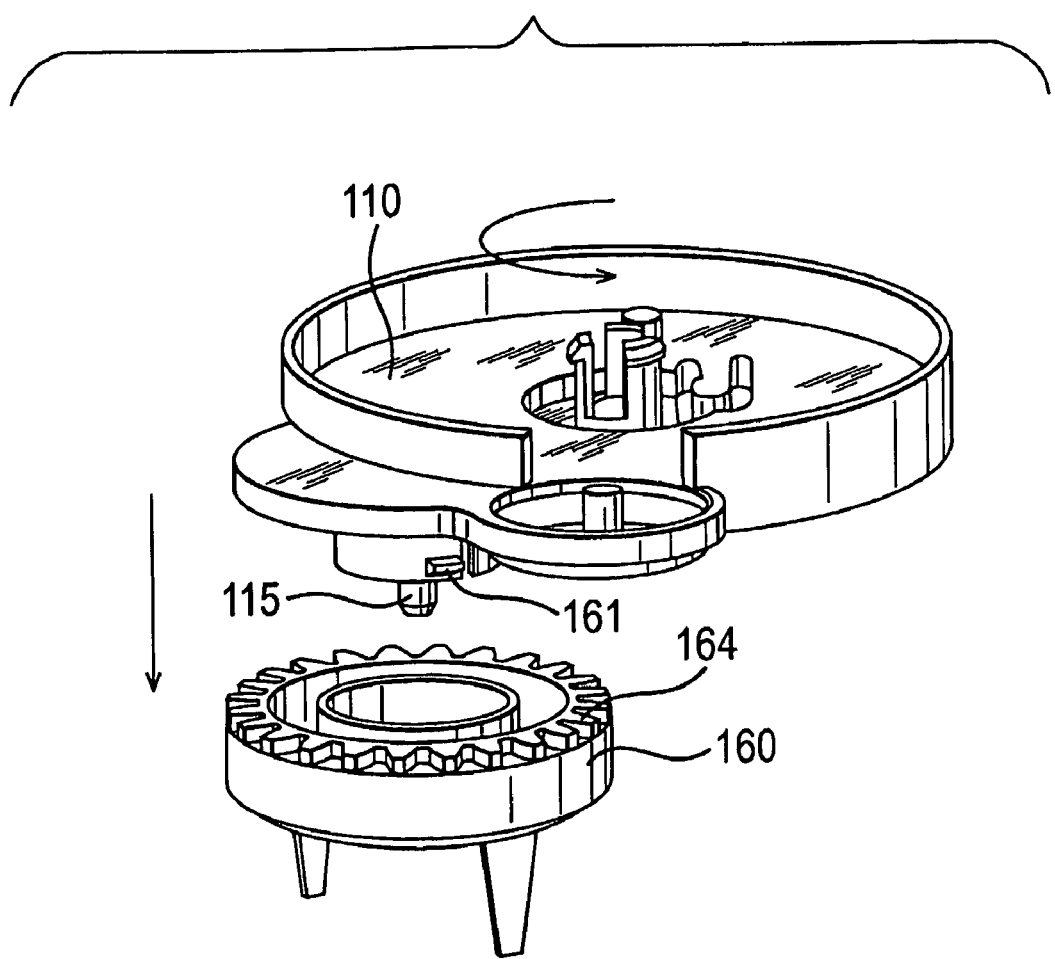

In a first assembly step of FIG. 10*a*, index wheel 160 having teeth 164 is mounted for rotation on downwardly protruding spindle mounting 115 of housing 110. A series of snap arms 161 (one only visible) hold the index wheel 160 in engagement with its mounting 115 on the housing 110.

Figure 10B:
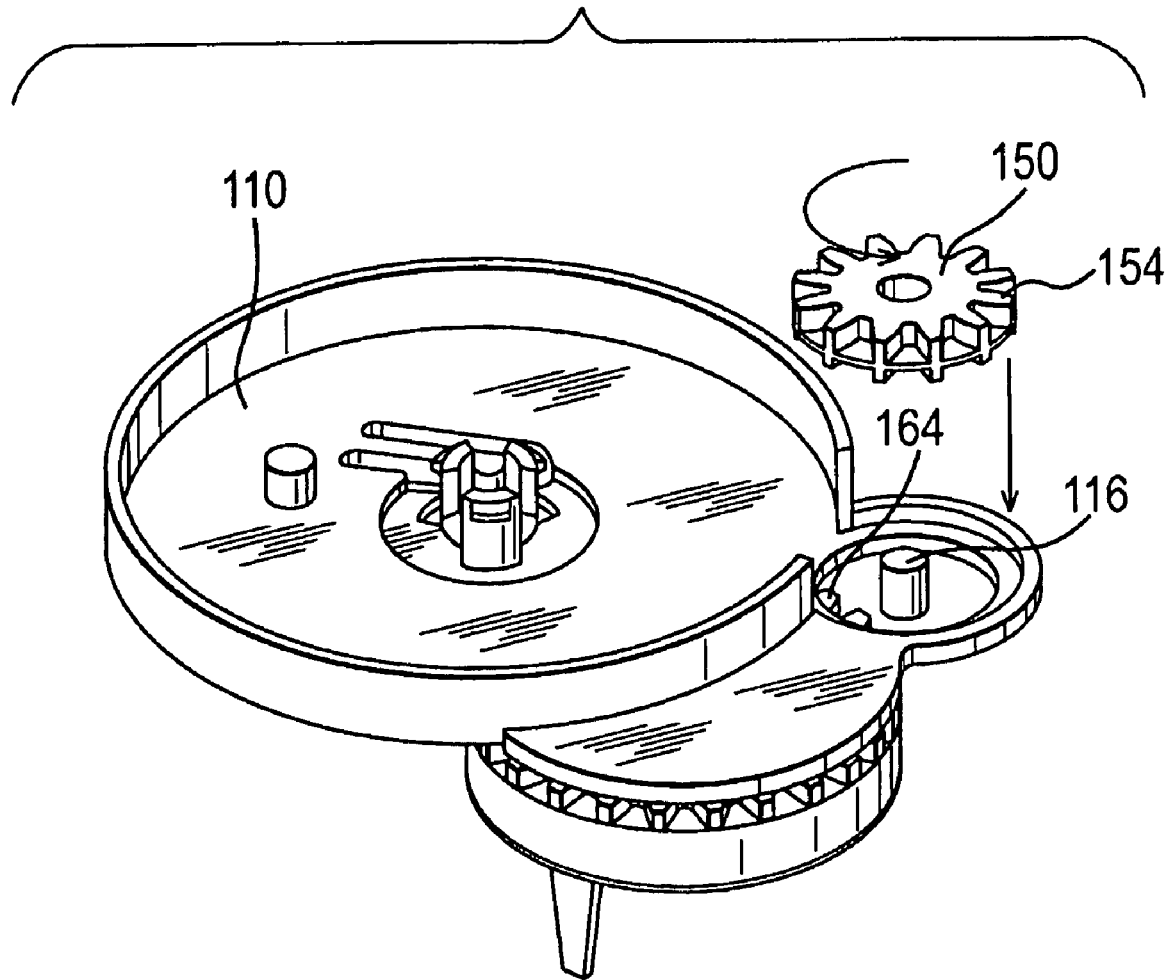

In the next assembly step of FIG. 10*b*, step up gear wheel 150 having teeth 154 is mounted for rotation on spindle 116 of the housing 110.

Figure 10C:
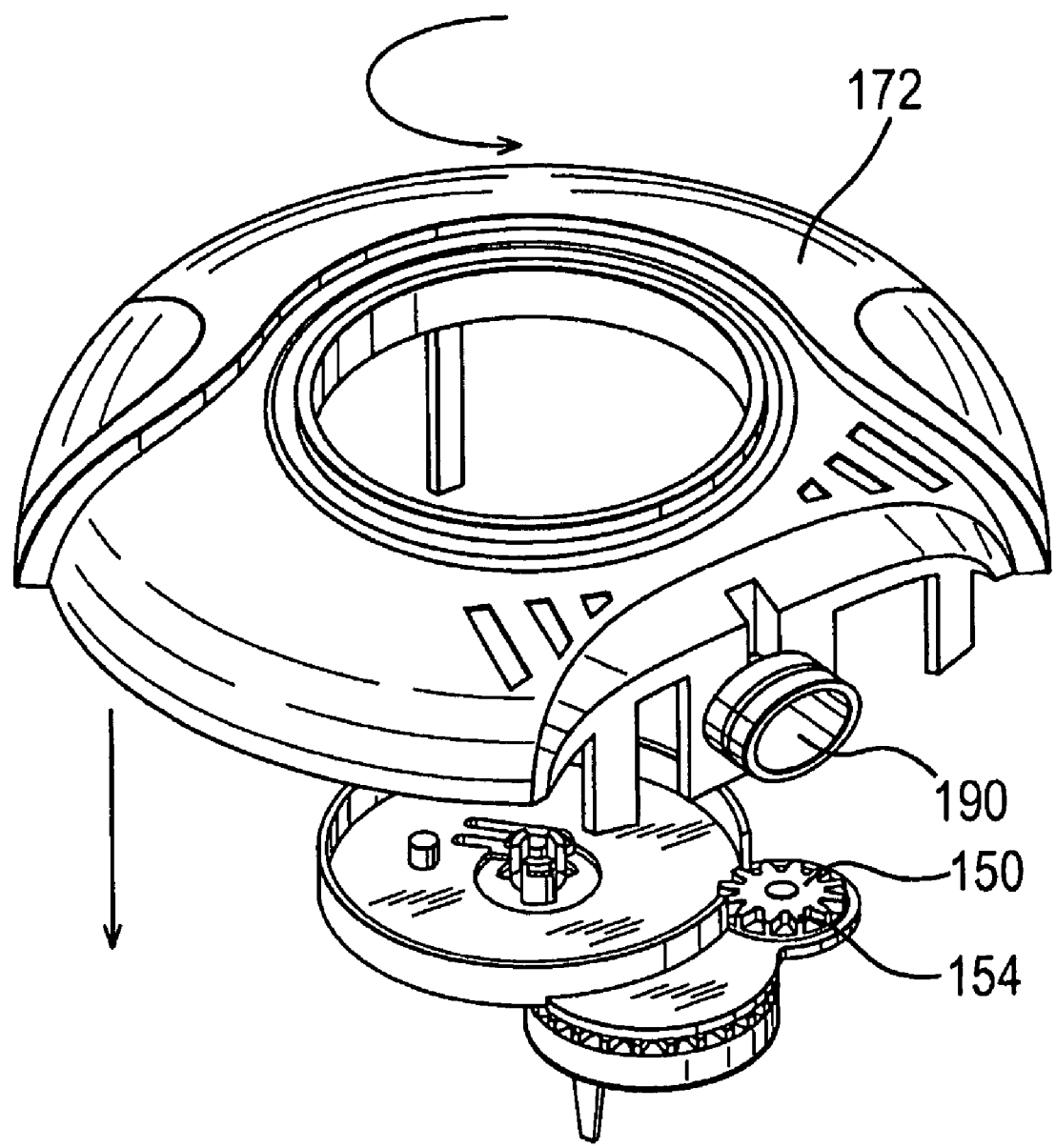

In the next assembly step of FIG. 10*c*, top cover 172 is snap-fitted to the sub-assembly of FIG. 10*b*. The top cover 172 may be seen to define an airflow tube 190 for receipt of a mouthpiece (not yet visible) in the finished inhaler.

Figure 10D:
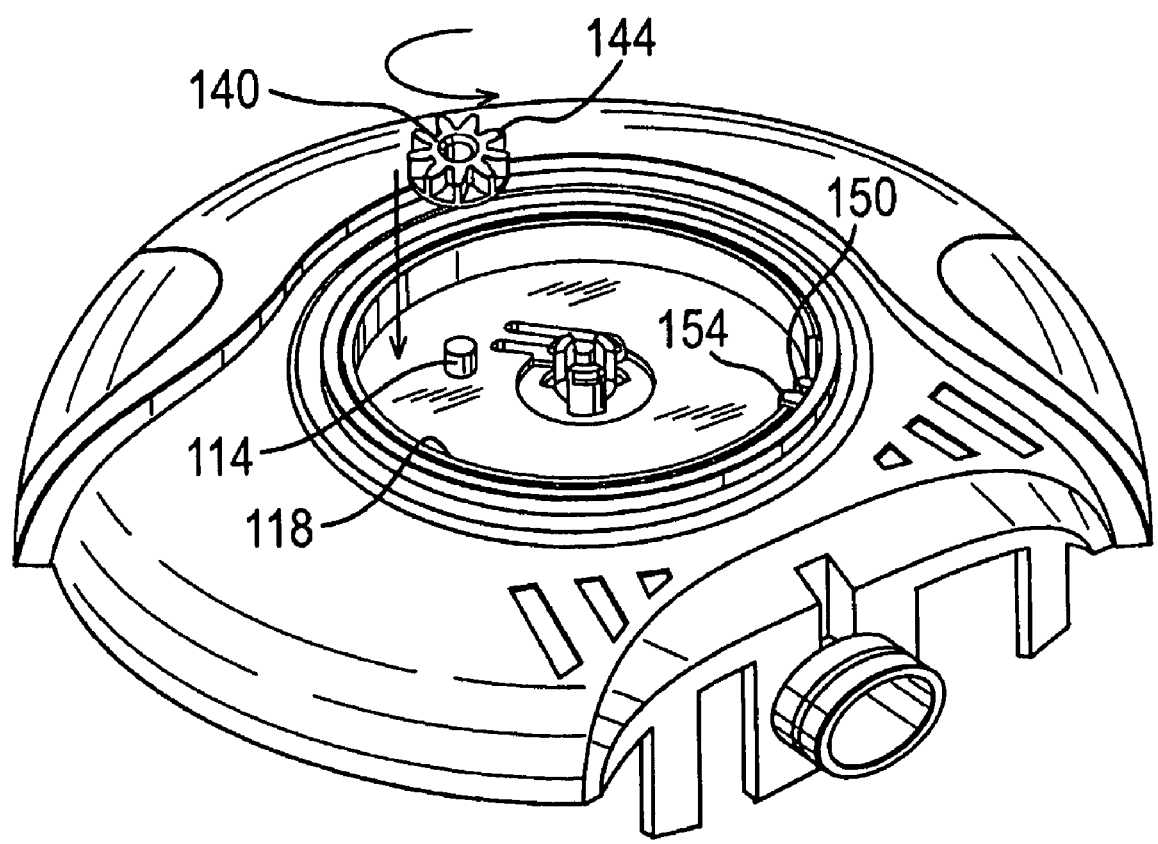

In the next assembly step of FIG. 10*d*, kick wheel 140 having teeth 144 is mounted for rotation on its spindle 114 within well 118 of the housing 110.

Figure 10E:
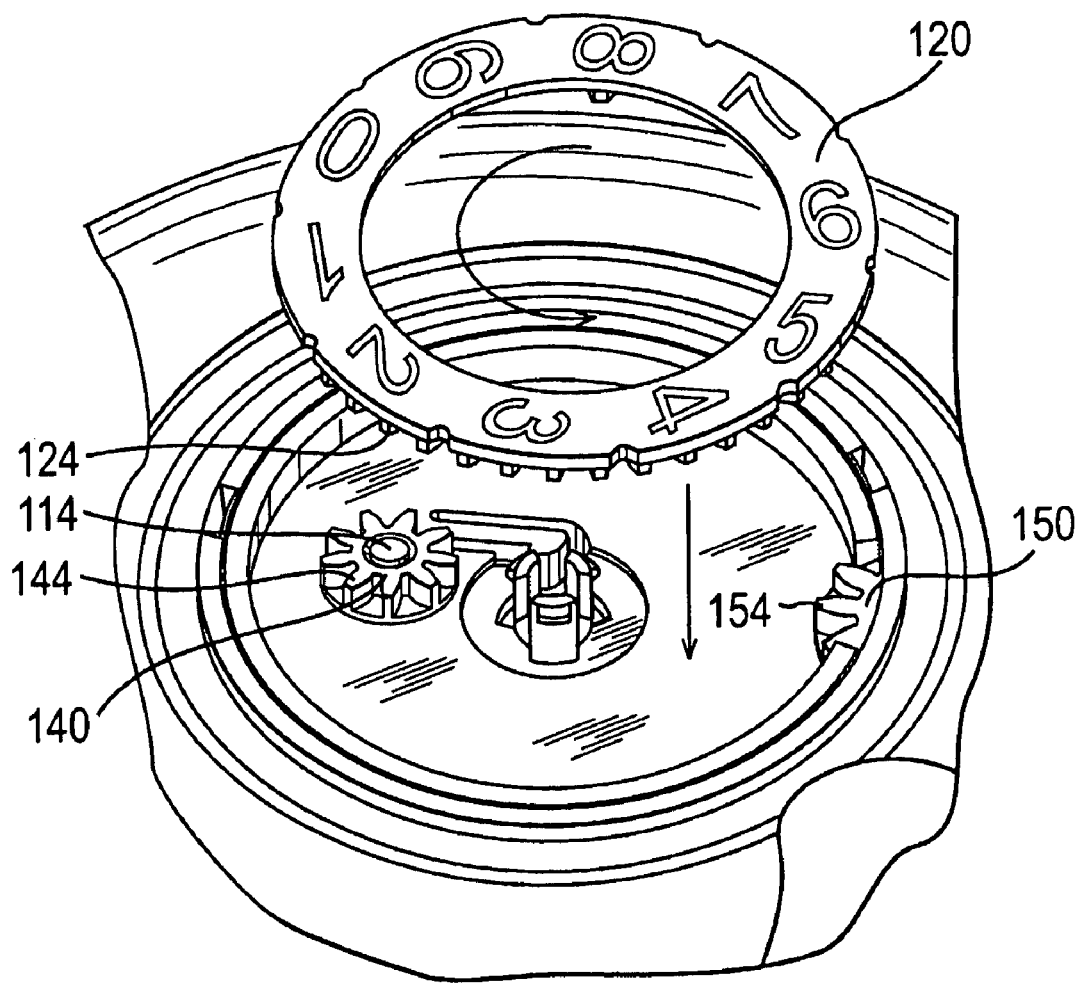

In the next assembly step of FIG. 10*e*, first, ring-shaped counter wheel 120 having teeth 124 is placed into the well 118 of the housing 110 such that its teeth 124 may mesh with those teeth 154 of the step up gear wheel 150. The teeth 144 of the kick gear wheel 140 are not engaged.

Figure 10F:
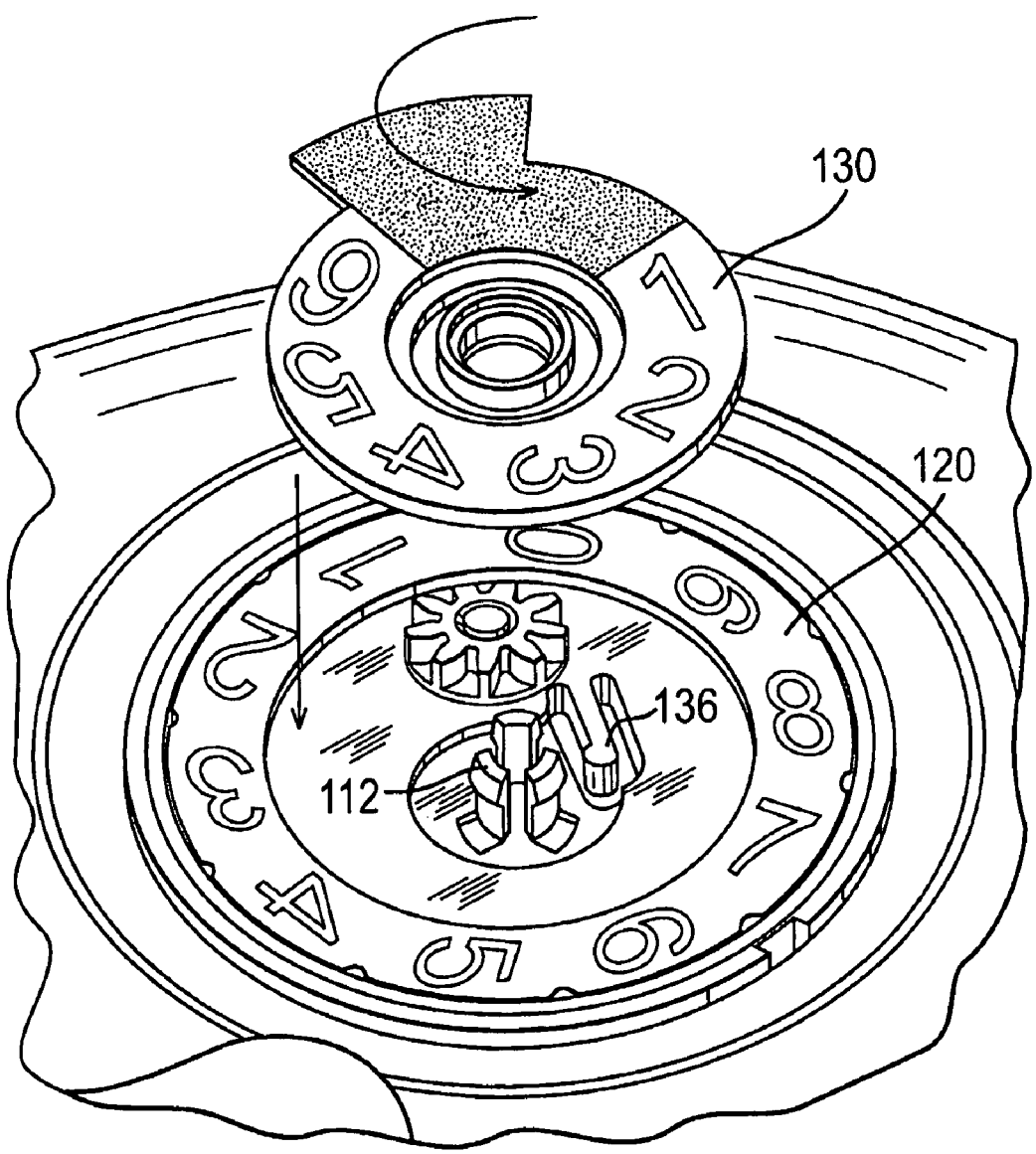

In the next assembly step of FIG. 10*f*, second counter wheel 130 is mounted for rotation on spindle 112 such that when in place it stands slightly proud from the level of the first counter wheel 120 (as in FIG. 8). Ratchet arm 136, engages cam profile 135 of flared star element 133 (not visible in FIG. 10*f*; but see FIG. 9) provided to the underside of second ('tens of units') count wheel 130 to prevent back running.

Figure 10G:
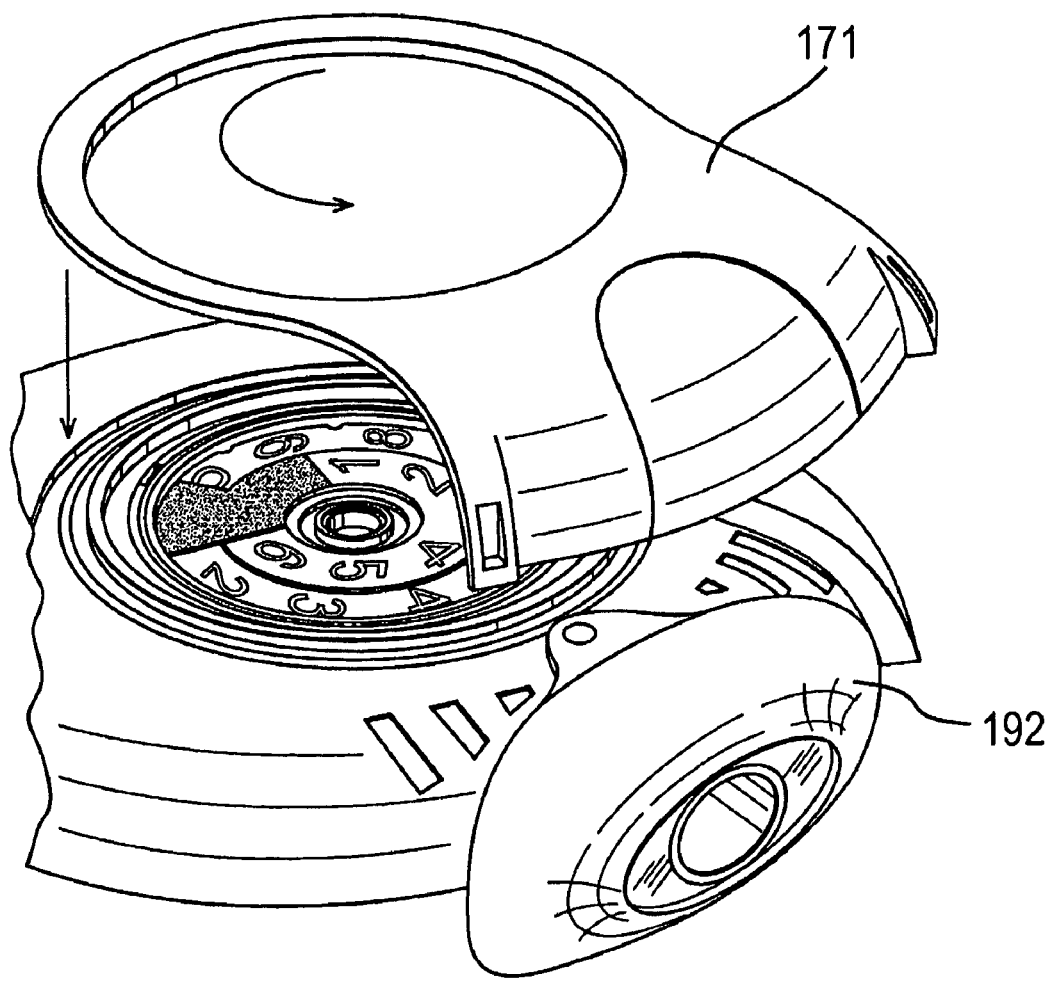

In the next assembly step of FIG. 10*g*, fascia 171 and mouthpiece 192 are applied to the sub-assembly of FIG. 10*f*.

The fascia 171, which acts as a 'mouthpiece cover' is mounted for rotation relative to the top cover 172.

Figure 10H:
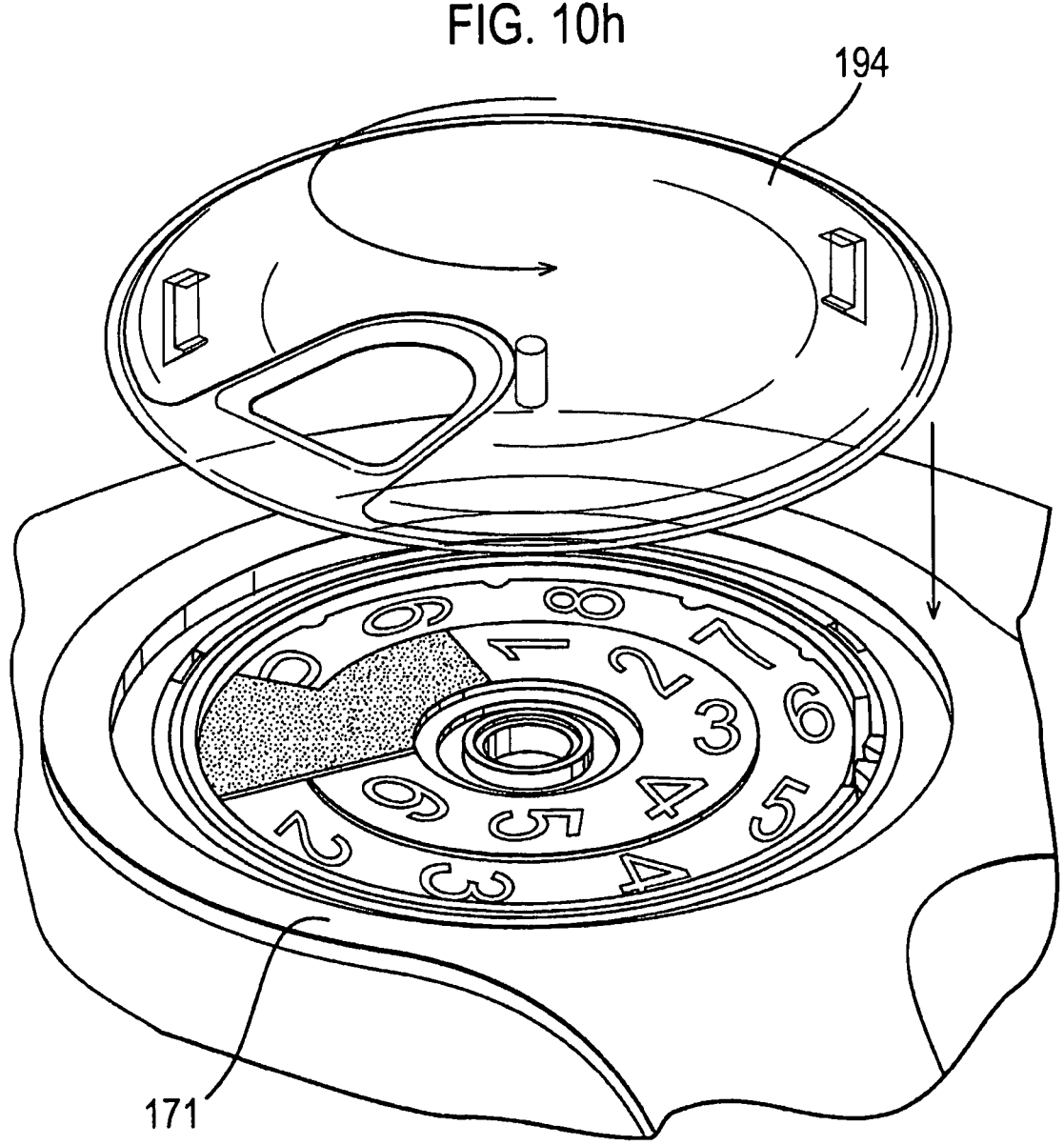

In the next assembly step of FIG. 10h, a clear plastic bezel 194 is applied to the fascia 171 of the sub-assembly of FIG. 10g.

In the final assembly step of FIG. 10i, the counter and top cover 172 sub-assembly of FIG. 10h is married up with a dry powder inhaler sub-assembly defined within a bottom cover 174. The top 172 and bottom 174 covers fixedly engage each other (e.g. in snap-fit or heat-sealed fashion).

The dry powder inhaler sub-assembly comprises an elongate, peelable blister strip 191 defining a series of blisters, each containing individual doses of inhalable medicament in dry powder form. The strip 191 is movable within the bottom cover 174 by means of a drive hub 193 that allows for sequential opening (i.e. by peeling off action) of each blister to allow the contents thereof to be made available at manifold 194 for inhalation by a patient at mouthpiece 192. When assembled, it may be appreciated that drive hub 193 is in meshed relationship with index wheel 160 such that drivable rotation of the drive hub 193 results in rotation of the index wheel 160, thereby resulting in both indexed advancement of the blister strip, as described above and advancement of the counter via step up gear 150 and interaction with the count mechanism, as described previously.

The dry powder sub-assembly is of a type generally known in the art and for example, described by U.S. Pat. Nos. 5,860,419, 5,873,360 and 5,590,645 in the name of Glaxo Group Ltd.

It will be appreciated that the assembly steps described above may either be carried out wholly at one location or be performed at separate locations. In one preferred aspect, the counter and top cover sub-assembly (assembled as shown in FIGS. 10a to 10h) is prepared in one location and supplied for marrying up with the bottom cover/dry powder inhaler sub-assembly at another location.

FIGS. 11a to 11e shows usage steps for using the dry powder inhaler device with second counter as produced by the assembly sequence of FIGS. 10a to 10i.

Figure 11A:
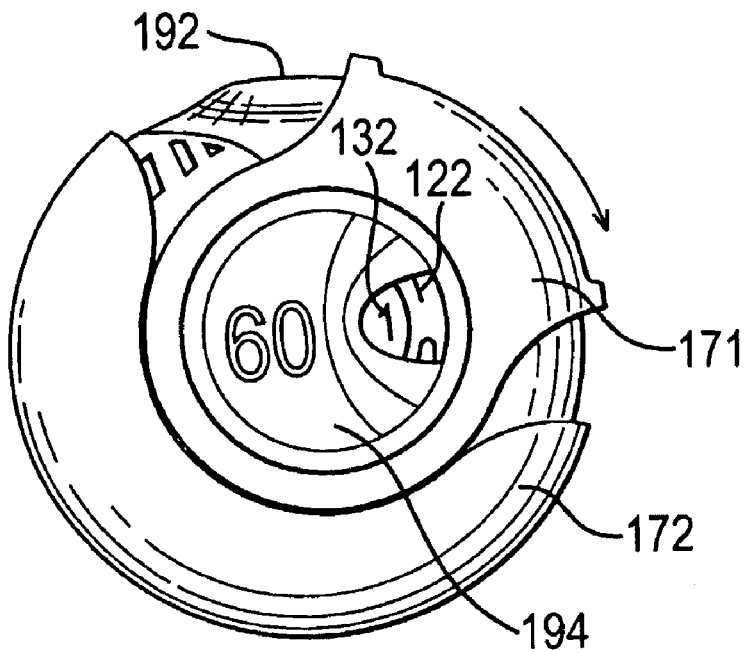
FIGS. 11a to 11f shows usage steps for using the dry powder inhaler device with second counter as assembled by the sequence of FIGS. 10a to 10i.

FIG. 11a shows a first priming step, in which fascia 171 and bezel 194 carried thereby are rotated with respect to the top 172 and bottom (not visible) covers to reveal the mouthpiece 192. This rotation is also geared (via index wheel 160 not visible) to both advance a blister pocket of the blister strip, thereby making a dry powder dose available and to advance the counter (via step up gear 150 not visible). As shown, the count, as represented by indicia 22, 32, is decreasing from '11' to '10', wherein in this case the count represents the number of doses remaining. The patient will then inhale through the mouthpiece 192 to receive the medicament dose.

Figure 11B:
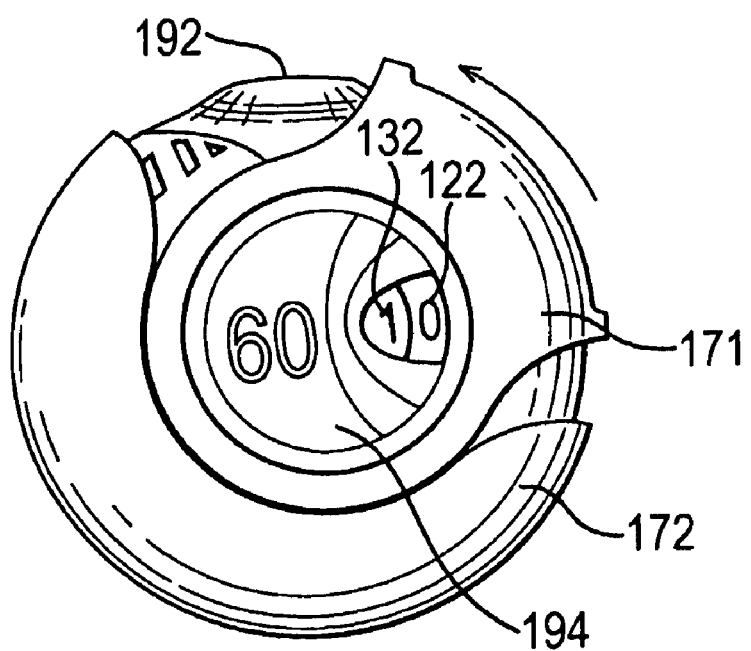

After patient use, and as shown at FIG. 11b, the fascia 171 is rotated in reverse fashion. Such reverse rotation results in no movement of either the blister strip or counter, which therefore does not count on.

Figure 11C:
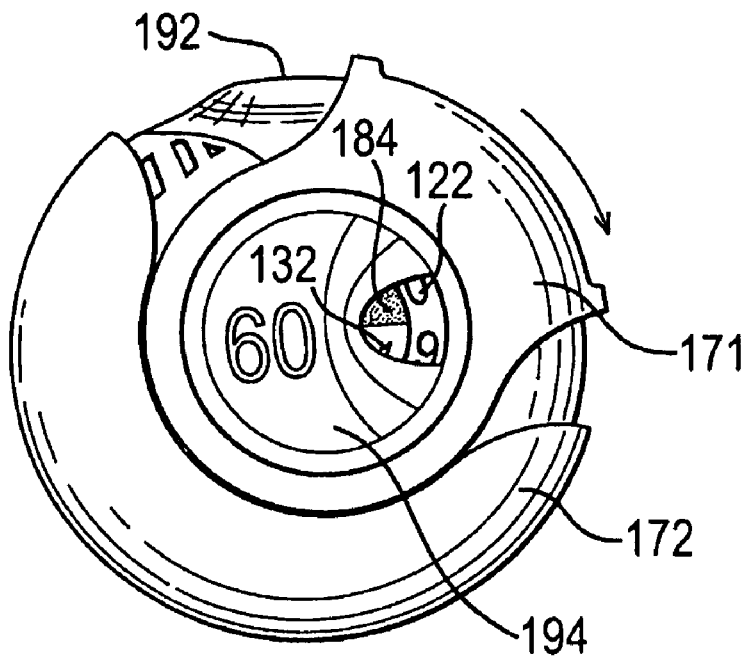

FIG. 11c shows the next priming step, in which fascia 171 and bezel 194 carried thereby are again rotated with respect to the top 172 and bottom (not visible) covers to reveal the mouthpiece 192. Again, this rotation both causes advancement of a blister pocket of the blister strip, thereby making a dry powder dose available and advances the counter. As shown, the count, as represented by coloured portion 180 and 'units' indicium 122, now decreasing from '10' to 'red 9'. The red colour gives the patient an early warning that only a few doses remain in the inhaler. Again, the patient will then inhale through the mouthpiece 192 to receive the medicament dose.

Figure 11D:
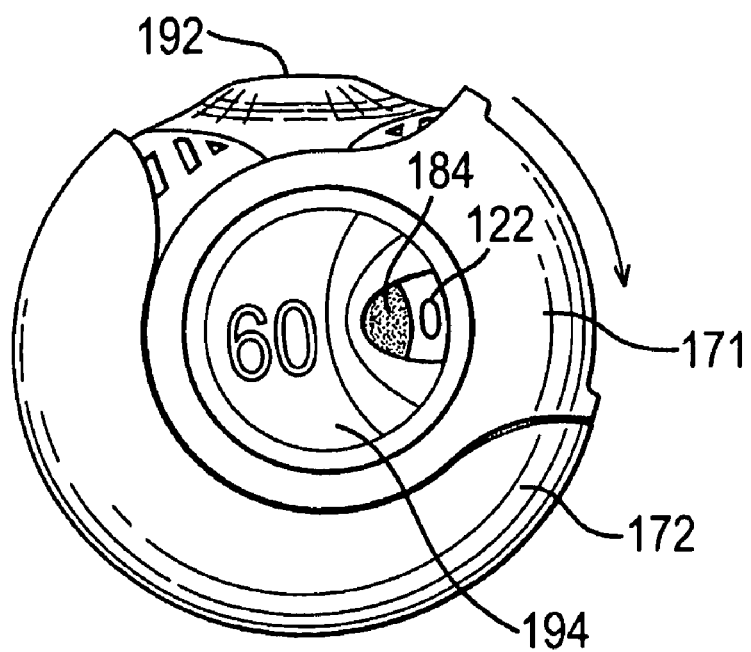

FIG. 11d shows the ultimate priming step, in which fascia 171 and bezel 194 carried thereby are again rotated with respect to the top 172 and bottom (not visible) covers to reveal the mouthpiece 192. This rotation causes advancement of the final blister pocket of the blister strip, thereby making the final dry powder dose available and advances the counter. As shown, the count, as represented by coloured portion 180 and 'units' indicium 122, now decreasing to 'red 0'. Again, the patient will then inhale through the mouthpiece 192 to receive the medicament dose. The inhaler is now empty.

Figure 11E:
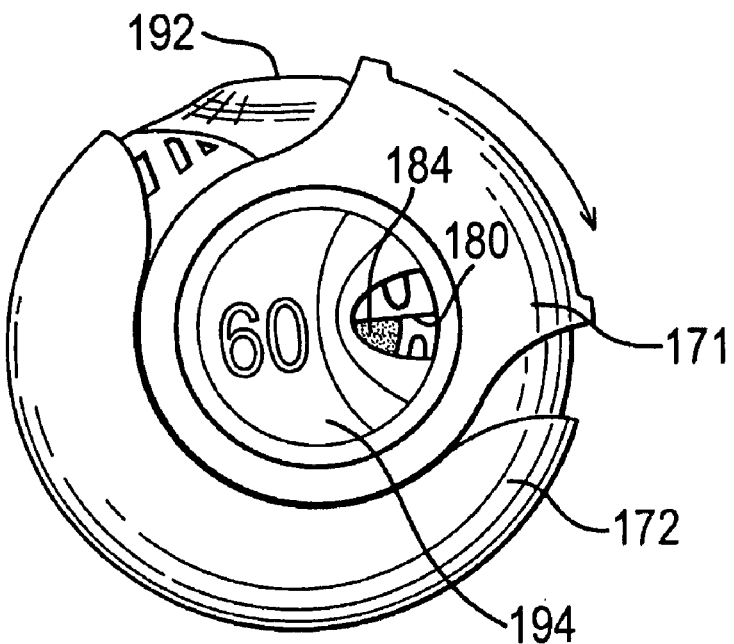
Figure 11F:
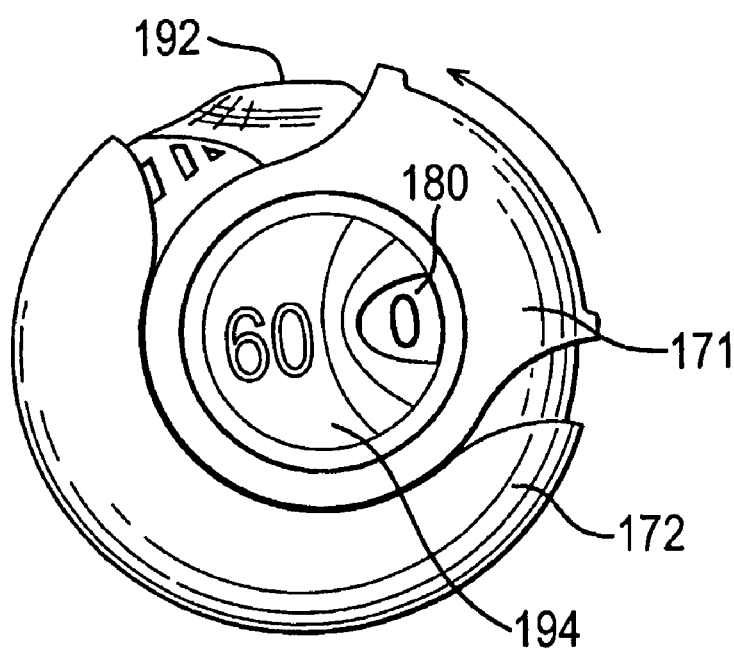

FIG. 11e shows what happens if the patient continues trying to prime the inhaler after the final dose has been made available. Rotation of the fascia 171 and bezel 194 carried thereby with respect to the top 172 and bottom (not visible) causes shutter 180 (herein marked with a prominent '0' indicium) on the second count wheel 130 to be drawn into a 'count obscured' position of FIG. 11f. However, as a result of the missing drive tooth at the stop position 138 of the second count wheel 130, any further rotation of the fascia 171 and bezel 194 has no effect on the second count wheel 130, and therefore once in place, the shutter 180 remains so. Any 'count' resulting from movement of the first counter wheel 120 is therefore obscured by the shutter. The blister strip may be further advanced within the inhaler a few more increments, but no medicament is made available because the final blister has already been opened.

Figure 12:
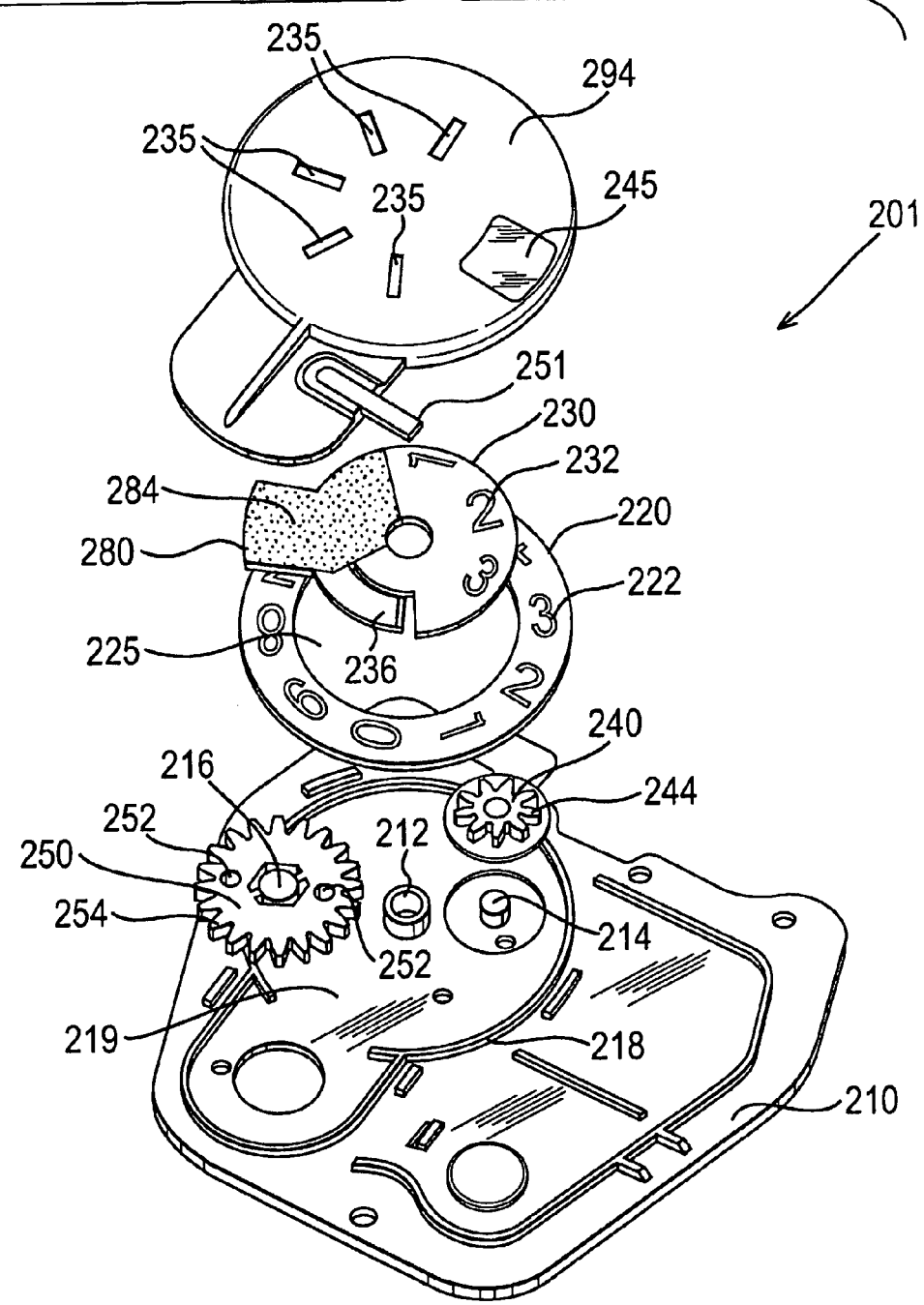
FIG. 12 shows an exploded view of a third dose counter in accord with the present invention.

FIG. 12 shows a third dose counter assembly 201 herein suitable for provision in sub-assembly form to a medicament dispenser for use therewith. In the following, the dose counter assembly 201 will be described as if used in conjunction with the medicament dispenser 470 shown and described with reference to FIG. 6a, although this is not to be taken as limiting as the counter 201 could as easily be used with other suitable medicament dispensers.

Figure 13B:
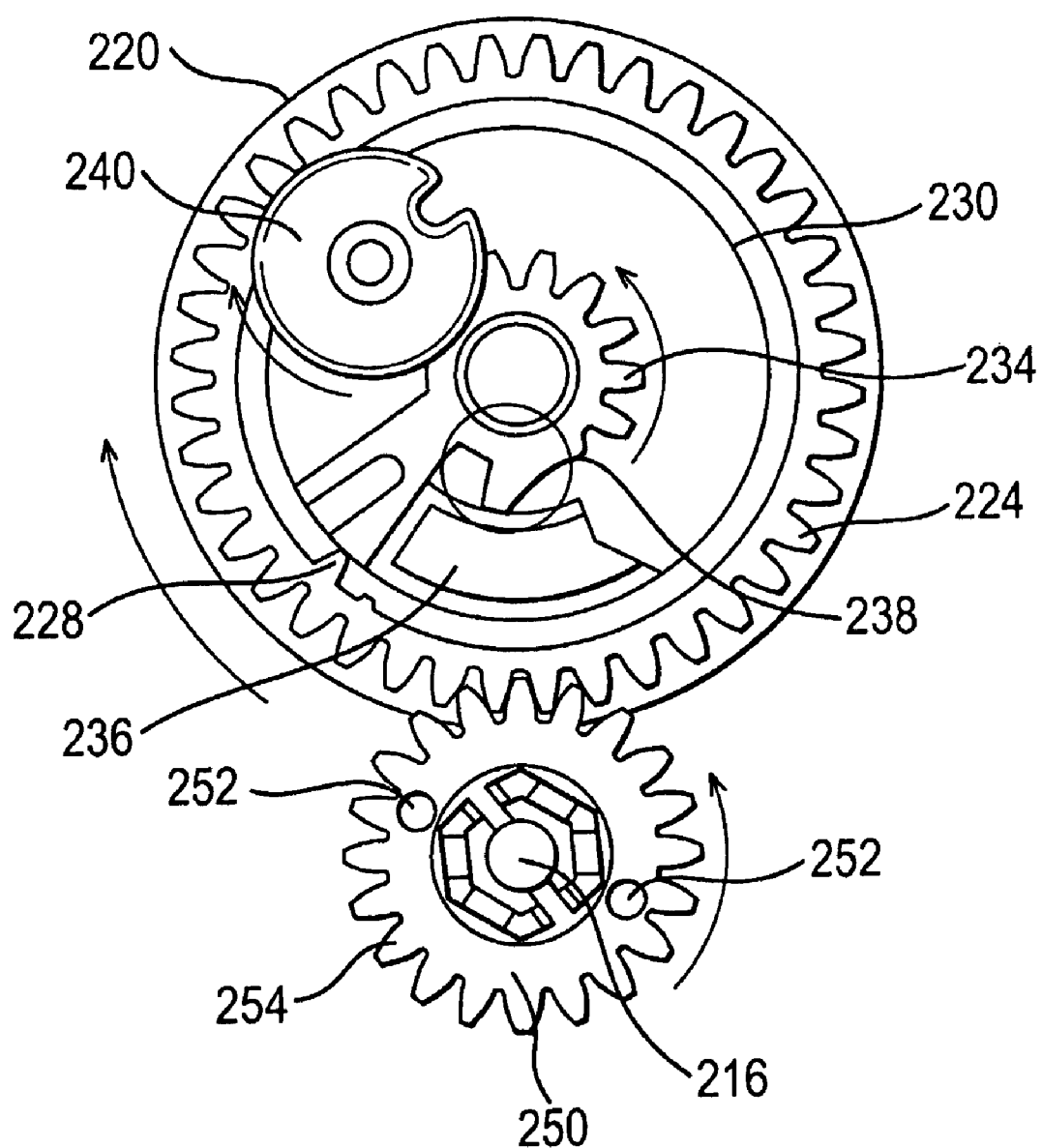
FIG. 13b shows a plan view from below of the count wheels of the third dose counter of FIG. 12.

FIGS. 13a and 13b respectively show top and bottom views view of the first 220 and second 230 count wheel parts of the assembly of FIG. 12.

In more detail, the dose counter assembly 201 comprises a base plate 210 provided with first 212, second 214 and third 216 spindle mountings, each capable of defining an axis of rotation and a circumferential wall 218 defining a circular retainer 219. First, ring-shaped count wheel 220 has 'units' count indicia 222 provided at spaced intervals on a top face thereof and a set of primary drive teeth 224 arranged circumferentially on the underside thereof (only visible on FIG. 13b). Second, circular form count wheel 230 also has three 'tens of units' count indicia 232 provided at spaced intervals on a top face thereof and a set of secondary drive teeth 234 provided in annular arrangement to the underside thereof (again, only visible on FIG. 13b). It may be noted that at stop position 238, the secondary drive teeth 234 are removed. The reason for this will become clear from the later description. The second count wheel 230 is also provided with coloured portion 284 and protruding shutter 280, which in this embodiment is of the same colour as the coloured portion, for instance red. Kick wheel 240 has kick teeth 244 provided in annular arrangement at the top face thereof.

When assembled, first count wheel 220 is received for rotation within circular retainer 219 and second count wheel 230 is received within the inner ring void 225 defined by ring-shaped first count wheel 220 and by first spindle 212 such that clearance exists between the first 220 and second 230 count wheels. Thus, the first 220 and second 230 count wheels are in concentric relationship with the level of the second count wheel 230 slightly raised relative to that of the first count wheel 220 to enable shutter 280 to protrude over and above the first count wheel 220. Both wheels 220, 230 are rotatable about a common axis of rotation defined in combination by the axis of first spindle 212 and the shape of the circular retainer 219. As shown, the first 220 and second 230 wheels rotate counter to each other (i.e. one clockwise, the other anti-clockwise). Kick wheel 240 is received by second spindle 214 for rotation thereabout (i.e. at a second axis of rotation defined by the second spindle 214 and therefore offset from the first axis of rotation). The set of kick teeth 244 of the kick wheel are in meshed relationship with the set of secondary drive teeth 234 of the second count wheel 230 such that rotary motion of the kick wheel 240 results in rotary motion of the second count wheel 230. In turn, gear teeth 254 of drive wheel 250 mesh with the primary drive teeth 224 of the first count wheel 220 for drivable rotation of the first count wheel 220. When the dose counter 201 is used with the medicament dispenser 470 of FIG. 6*a*, the drive wheel 250 is drivable by base spool take-up drive 460*a* as described previously.

The counter sub-assembly 201 is provided with a locking pin 251, which protrudes through one of a pair of apertures 252 in the drive wheel 250 to lock the drive wheel 250, thereby preventing any counts being recorded during transit of the counter sub-assembly 201. In a typical manufacturing operation, the sub-assembly 201 is therefore assembled and locking pin 251 inserted to lock drive wheel 250. The locked sub-assembly 201 is then transported for loading into a suitable medicament dispenser for use therewith. After loading, the locking pin 251 is removed such that the drive wheel 250 is now responsive to a suitable drive of the medicament dispenser.

First count wheel 220 may also be seen to be provided at its underside (see FIG. 9) with a fixed index tooth 228 arranged for intermittent meshing with the kick teeth 244 of the kick wheel 240 such that rotary motion of the kick wheel 240 results from rotary motion of the first count wheel 220 only when said intermittent meshing occurs.

Locating above the counter wheels 220, 230 there is provided a bezel/lens unit 294. The bezel 294 is provided with a plurality of downwardly protruding, cammed sections 235 that selectively interact with a ratchet element 236 of the second count wheel 230. The cammed sections 235 (which in effect, act as pawls to the ratchet element 236) act in combination with the ratchet element 236 such as to prevent reverse rotation of the second count wheel 230 as a result e.g. of patient tampering or due to the effects of undesirable vibration or impact.

The bezel 294 is further provided with a see-through region, or viewing window, 245 in which the count wheels 220, 230 display the count indicia 222, 232 representing the dose count. The locking pin 251 is also comprised in the bezel 294.

As shown in FIGS. 12 and 13*a*, the ratchet element 236 is configured as a resilient arcuate finger disposed at the outer circumference of the second count wheel 230. The ratchet element 236 has an upwardly-directed ratchet tooth 236*a* at the tip of the finger. The ratchet tooth 236*a* selectively interacts with the cammed sections 235 as the second count wheel 230 rotates to prevent reverse rotation thereof. The second count wheel 236 in this embodiment is integrally formed with the ratchet member 236 and the shutter 280.

As shown, the third counter assembly 201 is arranged to count down. Thus, in a first use operation of the medicament dispenser 470 of FIG. 6*a*, base spool take-up drive 460*a* is rotated in response to user action in indexing a dose within the medicament dispenser 470 thereby causing the drive gear 250 to rotate which, in turn, results in rotation of the first count wheel 220. The gearing of base take-up drive 460*a*, step up gear wheel 250 and first count wheel 220 is arranged such that when a single dose from first strip 491*a* is indexed by actuation of the base take-up drive 460*a*, first count wheel 220 rotates by 36° such that a single indicium 222 thereon is advanced (i.e. the 'units' count in the window 245 moves down one unit).

Where the previous visible count in the window 245 was x0 (e.g. 30 or 20), the counting action resulting from the use operation is subtly different. Once again, base take-up drive 460*a* is rotated in response to user action causing drive gear 250 to cause rotation of the first count wheel 220 by 36° such that the 'unit' indicium 222 in the window 245 moves on from '0' to '9'. This rotation of the first count wheel 220 however, also brings the index tooth 228 into meshed relationship with the kick teeth 244 of kick wheel 240 such that the kick wheel 240 rotates and in turn, the second count wheel 230 rotates. As best seen in FIG. 13*a*, the gearing of the relevant wheels 220, 230, 240 is arranged such that the second count wheel 230 rotates by 360/7° (that is to say by 360/n° wherein n is the number of relevant spacings) such that a single indicium 232 thereon is advanced (i.e. the 'tens' count in the window 245 moves down exactly one unit). It will be noted that the third counter assembly 201 is arranged to count down from '30' to '0' and then for the count to be blocked out.

Where the previous visible count was 10 (i.e. x=1), the counting action resulting from the use operation is again subtly different in that the kick wheel 240 action, as described above, results in the coloured (e.g. red) portion 284 of the second count wheel 230 being advanced into place in the window 245 such that the next display is 'red 9' (i.e. coloured portion 284; and indicia 222 is number 9).

Where the previous visible count was 'red 0' (i.e. x=0), the counting action resulting from the use operation is still again subtly different in that the kick wheel 240 action, as described above, results in the shutter portion 280 of the second count wheel 230 being advanced into place such that the next display in the window 245 is fully shuttered off (i.e. no indicia 222, 232 visible at all). Additionally, the stop position 238 in the set of secondary drive teeth 234 is brought into opposed relation with the kick teeth 244 whereby the kick teeth 244 and the secondary drive teeth 234 no longer mesh. Thus, if the first count wheel 220 continues to rotate, e.g. in response to continued user operation of a medicament dispenser into which the dose counter is incorporated, notwithstanding that all medicament doses have been dispensed, the index tooth 228 of the first count wheel 220 will still intermittently mesh with the kick teeth 244 to cause the kick wheel 240 to rotate. However, this rotation of the kick wheel 240 will not be transmitted to the second count wheel 230, due to the stop position 238, and the shutter 280 remains in the shuttering position.

It will be appreciated that the above usage of the second counter has been described in terms of a counter assembly 201 arranged to count downwards (i.e. to count on from 'n+1' to 'n' on indexing), but that the counter assembly may be straightforwardly modified to count upwards (i.e. instead to count on from 'n' to 'n+1' on indexing).

The components of the counter and any assemblies and sub-assemblies described above may be made from any suitable materials such as plastic polymer materials (e.g. acetal or ABS).

Whilst the dose counter herein has been mainly illustrated for use with a medicament dispenser in which an elongate form blister strip is advanced to enable release of medicament from the individual blisters thereof the dose counter is also suitable for use with other types of medicament dispenser. Thus, the dose counter is also suitable for use with metered dose inhaler (MDI) type devices in which, generally actuation is responsive to an actuating movement (e.g. push down the MDI canister) relative to its housing; reservoir dry powder inhalers (RDPI) and reservoir liquid spray inhalers (RLSI) in which, generally metering is responsive to an metering movement (e.g. bring metering cavity into communication with the bulk reservoir) relative to the bulk reservoir; and other types of multi-dose dry powder inhalers (MDPI) in which, generally dose advancement to a delivery position is responsive to a dose advancement movement (e.g. advancing a blister pack to move the next blistered dose to the delivery position) relative to a housing. Suitable medicament dispensers herein are for the dispensing of medicament, particularly for the treatment of respiratory disorders such as asthma and chronic obstructive pulmonary disease (COPD), bronchitis and chest infections. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or $6\alpha, 9\alpha$-difluoro-11$\beta$-hydroxy-16$\alpha$-methyl-3-oxo-17$\alpha$-propionyloxy-androsta-1, 4-diene-17$\beta$-carbothioic acid S-(2-oxo-tetrahydro-furan-3-yl)ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred components of the combinations comprise medicaments selected from albuterol, salmeterol, fluticasone propionate and beclomethasone dipropionate and salts or solvates thereof, e.g., the sulphate of albuterol and the xinafoate of salmeterol.

Preferred components of combinations of active ingredients contain salbutamol (e.g., as the free base or the sulphate salt) or salmeterol (e.g., as the xinafoate salt) or formoterol (eg as the fumarate salt) in combination with an anti-inflammatory steroid such as a beclomethasone ester (e.g., the dipropionate) or a fluticasone ester (e.g., the propionate) or budesonide. A particularly preferred combination of components comprises fluticasone propionate and salmeterol, or a salt thereof (particularly the xinafoate salt). A further combination of components of particular interest is budesonide and formoterol (e.g. as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

It will be understood that the present disclosure is for the purpose of illustration only and the invention extends to modifications, variations and improvements thereto.

The present application claims priority from UK patent application Nos. 0 403 394.0 and 0 418 264.8 filed, respectively, on 16 Feb. 2004 and 16 Aug. 2004, the entire contents of each of which are incorporated herein by reference.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A dose counter for use with a medicament dispenser, said dose counter comprising
   a first count wheel arranged to rotate about a first axis of rotation, said first count wheel including count indicia and a set of primary drive teeth arranged annularly thereon for drivable rotation of the first count wheel about said first axis of rotation;
   a second count wheel arranged to rotate about the first axis of rotation, said second count wheel including count indicia and a set of secondary drive teeth arranged annularly thereon, and said second count wheel is arranged concentric to the first count wheel such that the respective count indicia are arranged concentrically;
   a kick wheel arranged to rotate about a second axis of rotation offset from the first axis of rotation, said kick wheel including a set of kick teeth arranged annularly thereon and in meshed relationship with the set of secondary drive teeth of the second count wheel such that rotary motion of the kick wheel results in rotary motion of the second count wheel; and, a drive wheel which is constantly in meshed relationship with the primary drive teeth of the first count wheel and which is adapted in use to couple with an operating mechanism of a medicament dispenser such that actuation of the operating mechanism will cause the drive wheel to rotate and to drive rotation of the first count wheel;

wherein said first count wheel further includes a fixed index tooth arranged for intermittent meshing with the kick teeth of the kick wheel such that rotary motion of the kick wheel results from rotary motion of the first count wheel only when said intermittent meshing occurs;

wherein the dose counter has a display region through which the count indicia of the first and second count wheels are rotatable;

wherein the second count wheel comprises a shutter which is movable to a shuttering position in which it shutters the display region;

wherein the dose counter is configured and arranged to display a count sequence in the display region with the count indicia and to cause the shutter to move to its shuttering position at the end of the count sequence; and wherein the dose counter is configured and arranged so that drive transmission from the first count wheel to the second count wheel through the kick wheel is disengaged when the shutter is in the shuttering position to keep the shutter in the shuttering position when the drive wheel drives further rotation of the first count wheel.

2. The dose counter of claim 1, wherein the count indicia of the first count wheel are on a face which has the form of a ring and the second count wheel is disposed within the ring.

3. The dose counter of claim 2, wherein the first count wheel is a ring.

4. The dose counter of claim 2, wherein the count indicia of the second count wheel are on a face which is received in the inner ring void of the face of the first count wheel.

5. The dose counter of claim 4, wherein the shutter is formed by the face of the second count wheel.

6. The dose counter of claim 5, wherein the shutter extends outwardly from the face to overlie the count indicia of the first count wheel.

7. The dose counter of claim 4, wherein the face of the second count wheel further forms a ratchet for interacting with pawls to prevent reverse movement of the second count wheel.

8. The dose counter of claim 7, wherein the ratchet is a resilient finger forming an outer peripheral segment of the face.

9. The dose counter of claim 8 further having a housing on which the pawls are disposed.

10. The dose counter of claim 7 further having a housing on which the pawls are disposed.

11. The dose counter of claim 4, wherein the first count wheel has a circular form.

12. The dose counter of claim 1, wherein the drive wheel is arranged to rotate about a third axis of rotation offset from the first and second axes and wherein the first, second and third axes are essentially parallel.

13. The dose counter of claim 1 adapted for use with a medicament dispenser as an insert thereto and having a base plate on which the count wheels, kick wheel and drive wheel are rotatably mounted.

14. The dose counter of claim 13 having a bezel mounted to the base plate to cover the count wheels, the kick wheel and the drive wheel.

15. The dose counter of claim 14, wherein the bezel has a viewing window for viewing the count sequence.

16. The dose counter of claim 12, wherein the first count wheel has a ring member having inner and outer surfaces on which the index tooth and primary drive teeth are respectively provided, wherein the second count wheel is nested in the ring member such that the secondary drive teeth face the inner surface of the ring member and wherein the kick wheel is located between the inner surface of the ring member and the secondary drive teeth.

17. The dose counter of claim 1, wherein the second axis of rotation is spaced from the first axis of rotation at a spacing such that the path of rotation defined by the kick teeth of the kick wheel is enclosed by the path of rotation defined by the primary drive teeth of the first count wheel.

18. The dose counter of claim 1, wherein the index tooth is fixed at a point at or about the circumference of the first count wheel and rotation of the first count wheel is arranged to bring the index tooth into meshed relationship with the kick teeth of the kick wheel at a particular point of the rotary cycle of the first count wheel such that meshing occurs once during each complete rotation of the first count wheel.

19. The dose counter of claim 1 adapted for use with a medicament dispenser as an insert thereto.

20. The dose counter of claim 1 having a housing which includes a viewing window through which the count sequence may be viewed.

21. The dose counter of claim 1, wherein the second count wheel is integrally formed with the shutter.

22. The dose counter of claim 1, wherein the shutter overlies count indicia of the first count wheel.

23. The dose counter of claim 1, configured and arranged such that meshing of the kick teeth with the index tooth and/or the secondary drive teeth is unable to occur when the shutter is in its shuttering position.

24. The dose counter of claim 23, wherein a gap is provided in the set of kick teeth or the secondary drive teeth to disable meshing when the shutter is in its shuttering position.

25. The dose counter of claim 1, wherein the shutter is a protrusion of the second count wheel which protrudes in a radial direction with respect to the first axis of rotation.

26. The dose counter of claim 24, wherein the gap is provided in the secondary drive teeth.

27. The dose counter of claim 1, wherein the index tooth is the only index tooth of the first count wheel.

* * * * *